United States Patent
Shiota et al.

(10) Patent No.: US 10,233,269 B2
(45) Date of Patent: *Mar. 19, 2019

(54) COMPOUND CONTAINING STRUCTURAL UNIT DERIVED FROM VINYL ETHER COMPOUND

(71) Applicant: TOKYO OHKA KOGYO CO., LTD., Kawasaki-shi (JP)

(72) Inventors: Dai Shiota, Kawasaki (JP); Kunihiro Noda, Kawasaki (JP); Hiroki Chisaka, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/780,743

(22) PCT Filed: Mar. 28, 2014

(86) PCT No.: PCT/JP2014/059308
§ 371 (c)(1),
(2) Date: Sep. 28, 2015

(87) PCT Pub. No.: WO2014/157674
PCT Pub. Date: Oct. 2, 2014

(65) Prior Publication Data
US 2016/0046742 A1    Feb. 18, 2016

(30) Foreign Application Priority Data

Mar. 29, 2013 (JP) .................................. 2013-075397

(51) Int. Cl.
*C08F 116/12* (2006.01)
*C07C 41/06* (2006.01)
(Continued)

(52) U.S. Cl.
CPC ............ *C08F 116/12* (2013.01); *C07C 41/06* (2013.01); *C07C 43/21* (2013.01); *C08F 16/32* (2013.01);
(Continued)

(58) Field of Classification Search
CPC ........ C08F 116/12; C08F 16/32; C08G 65/40; C08L 35/00; C09D 135/00; H01L 31/0392; H01L 31/048; H01L 33/56; Y02E 10/50
See application file for complete search history.

(56) References Cited

U.S. PATENT DOCUMENTS 4,069,056 A * 1/1978 Crivello ............ C08F 299/0428
423/461
4,473,626 A    9/1984 Molaire et al.
(Continued)

FOREIGN PATENT DOCUMENTS

CN    101685165 A    3/2010
EP    0428706 A1    5/1991
(Continued)

OTHER PUBLICATIONS

Felix et al., Proc. of SPIE, 2008, vol. 6923, pp. 69233L-1 to 69233L-11.*

(Continued)

*Primary Examiner* — Satya Sastri
(74) *Attorney, Agent, or Firm* — Knobbe Martens Olson & Bear LLP

(57) ABSTRACT

A compound containing a structural unit derived from a novel vinyl ether compound. This compound contains a structural unit represented by formula (1), in which the rings ($Z^1$, $Z^2$, $Y^1$, $Y^2$) are aromatic hydrocarbon rings; $X^1$ and $X^2$ represent a single bond or —S—; R represents a single bond or a specific divalent group; $R^{1a}$ and $R^{1b}$ represent a single bond or a C1-4 alkylene group; $R^{2a}$ and $R^{2b}$ represent a specific substituent group such as a monovalent hydrocarbon group; $R^{3a}$ and $R^{3b}$ represent a cyano group, a halogen atom, or a monovalent hydrocarbon; m1 and m2 are integers of 0 or greater; n1 and n2 are integers of 0-4; $V^1$ is a group represented by formulas (a1)-(a3); and $V^2$ is a group represented by formulas (a1)-(a4). In formulas (a1)-(a4), * represents a bonding hand, while  and * represent a bonding hand with an oxygen atom.

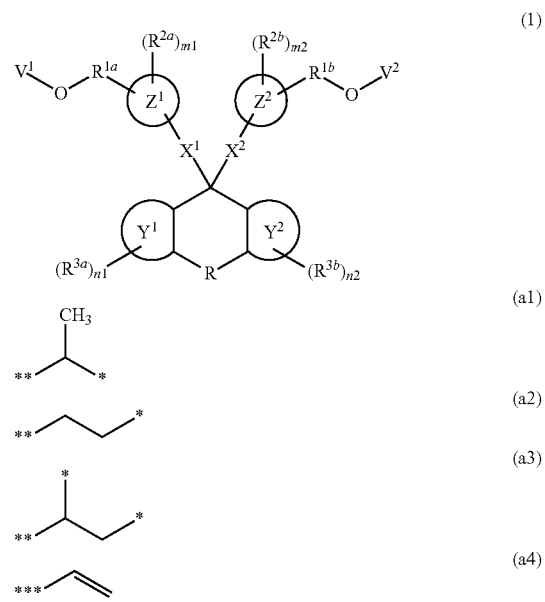

18 Claims, No Drawings

(51) Int. Cl.

| | | |
|---|---|---|
| *C07C 43/21* | (2006.01) | |
| *C08F 16/32* | (2006.01) | |
| *C08L 35/00* | (2006.01) | |
| *C09D 135/00* | (2006.01) | |
| *H01L 31/0392* | (2006.01) | |
| *H01L 31/049* | (2014.01) | |
| *H01L 31/048* | (2014.01) | |
| *C08G 65/00* | (2006.01) | |
| *H01L 33/56* | (2010.01) | |

(52) U.S. Cl.
CPC ............ *C08L 35/00* (2013.01); *C09D 135/00* (2013.01); *H01L 31/0392* (2013.01); *H01L 31/049* (2014.12); *H01L 31/0481* (2013.01); *C08G 65/002* (2013.01); *H01L 33/56* (2013.01); *Y02E 10/50* (2013.01)

(56) References Cited

U.S. PATENT DOCUMENTS

| | | | |
|---|---|---|---|
| 5,176,977 | A | 1/1993 | Molaire et al. |
| 7,534,547 | B2 * | 5/2009 | Hanabata ............... C07C 43/303 430/270.1 |
| 2003/0064168 | A1 | 4/2003 | Kato et al. |
| 2003/0211421 | A1 | 11/2003 | Hanabata et al. |
| 2004/0106004 | A1 | 6/2004 | Li |
| 2005/0158659 | A1 | 7/2005 | Lee |
| 2005/0175930 | A1 | 8/2005 | Lee |
| 2006/0166114 | A1 | 7/2006 | Lee |
| 2007/0008460 | A1 * | 1/2007 | Takeda ................. G02F 1/13362 349/98 |
| 2007/0117876 | A1 | 5/2007 | Lee |
| 2008/0220372 | A1 | 9/2008 | Lee et al. |
| 2009/0068569 | A1 | 3/2009 | Seta et al. |
| 2010/0076138 | A1 | 3/2010 | Iwasa |
| 2016/0046551 | A1 * | 2/2016 | Shiota ..................... C07C 69/54 558/46 |
| 2016/0046552 | A1 * | 2/2016 | Shiota ..................... C07C 69/54 430/288.1 |
| 2016/0046742 | A1 | 2/2016 | Shiota et al. |

FOREIGN PATENT DOCUMENTS

| | | | |
|---|---|---|---|
| EP | 0598552 A2 | | 5/1994 |
| EP | 2980057 A1 | | 2/2016 |
| EP | 2980058 A1 | | 2/2016 |
| EP | 2980059 A1 | | 2/2016 |
| JP | 2000-178115 A | | 6/2000 |
| JP | 2001106761 A | * | 4/2001 |
| JP | 2002-255929 A | | 11/2002 |
| JP | 2004-137262 | | 5/2004 |
| JP | 2006-152115 A | | 6/2006 |
| JP | 2006-282875 A | | 10/2006 |
| JP | 2006-327990 | | 12/2006 |
| JP | 2009-013096 A | | 1/2009 |
| JP | 2009-155253 A | | 7/2009 |
| JP | 2009-155256 A | | 7/2009 |
| JP | 2009155253 A | * | 7/2009 |
| JP | 2009-215447 | | 9/2009 |
| JP | 2010-037470 A | | 2/2010 |
| JP | 2010-097194 | | 4/2010 |
| JP | 2011-090774 A | | 5/2011 |
| JP | 2011-201791 | | 10/2011 |
| JP | 2012-063728 | | 3/2012 |
| JP | 2012063728 A | * | 3/2012 |
| JP | 2012-068652 A | | 4/2012 |
| JP | 2012-118551 A | | 6/2012 |
| JP | 2013-028574 | | 2/2013 |
| KR | 10-2003-0005419 A | | 1/2003 |
| WO | WO 90/15043 A2 | | 12/1990 |
| WO | WO 02/079131 | | 10/2002 |
| WO | WO 2006/132139 A1 | | 12/2006 |
| WO | WO 2013/018302 A1 | | 2/2013 |
| WO | WO2013022065 A1 | | 3/2015 |

OTHER PUBLICATIONS

Felix et al., Proc. of SPIE, 2008, vol. 6923, pp. 69233L-69233L-11.*
JP 2012063728 A, Mar. 2012, Derwent Ab.*
Encyclopedia of Polymer Science and Technology, vol. 10, Mar. 2004, pp. 807-836 (http://onlinelibrary.wiley.com/doi/10.1002/0471440264.pst490/pdf).*
JP 2001106761 A, Apr. 2001, Machine Translation.*
Bohumir Koutek, et al., Perturbation of the Fuchsone Chromophore by 3, 5-Methyl Substitusion. Sterically Crowded Exocyclic Double Bond, Collection of Czechoslovak Chemical Communications, 1981, 46(10), pp. 2540-56, p. 2547 Scheme 3.
Carrie Y. K. Chan et al: "Polycyclotrimerization of Dinitriles: A New Polymerization Route for the Construction of Soluble Nitrogen-Rich Polytriazines with Hyperbranched Structures and Functional Properties", Macromolecules, vol. 46, No. 24, Dec. 23, 2013 (Dec. 23, 2013), pp. 9494-9506, XP055251844, US.
Ching-Nan Chuang et al: "Synthesis and characterization of fluorene-derived PU as a thermo cross-linked hole-transporting layer for PLED", Polymer., vol. 53, No. 10, Apr. 1, 2012 (Apr. 1, 2012), pp. 2001-2007, XP055250560, GB.
Database CAPLUS [Online] Chemical Abstracts Service, Columbus, Ohio, US; XP002754507, retrieved from STN accession No. 80826-88-6P Database accession No. 1978:423387 & Lewis, Terry Warren Ti—Dehydration Reactions in the Organic Solid State: "Dehydration reactions in the organic solid state", INT, 1977.
Gyoo-Soon Park et al: "H-Bonding Controls the Regio-selectivities on the Acid-catalyzed Reaction of Fluorenone with Phenol Derivatives", Bulletin of the Korean Chemical Society, vol. 31, No. 7, Jul. 20, 2010 (Jul. 20, 2010), pp. 1837-1838, XP055251273, KR.
Hans-Dieter Becker, et al., Preparation and Reactions of 2, 6-Di-tert-butyl-4-(9-fluorenylidene)-1, 4-benzoquinone, Journal of Organic Chemistry, 1976, 41(2), pp. 214-221, Table II Compound 11 a.
Konrad H. Bleicher, et al., New phenylfluorenyl based linkers for solid phase synthesis, Tetrahedron Letters, 2000, 41(47), pp. 9037-9042, Scheme 1. Compound(4).
Marilia O. F. Goulart, et al., Electroorganic Reactions. 31. Quinonemethide Radical-Anions and Dianions: Their Cathodic Generation and Reactivity, Journal of Organic Chemistry, 1988, 53(11), pp. 2520-2525, p. 2521 Compound (23).
Martin Stiles, et al., Tribenzotropone from a 1, 3-Rearrangement, Journal of Organic Chemistry, 1957, 22, pp. 1243-1246, p. 1245 9-o-hydroxyphenyl-9-fluorenol.
Mitsuaki Yamada et al: "Synthesis of Fluorenebisphenoxy Derivatives by Acid-sulfur Compound Catalyzed Condensation Reaction", Chemistry Letters, Chemical Society of Japan, Japan, vol. 10, Jan. 1, 1998 (Jan. 1, 1998), pp. 1055-1056, XP002361848.
Sadaaki Nunomoto et al: "Properties of polymers cross-linked by a fluorene ring or siloxane-containing cross-linking agents", Designed Monomers and Polymers, vol. 4, No. 1, Mar. 1, 2001 (Mar. 1, 2001), pp. 1-8, XP055286865, NL.
Shoji Kajigaeshi et al: "Spirofluorenes. V. Synthesis of spirofluorenes containing o-phenylene group in their system.", Nippon Kagaku Kaishi: Journal of the Chemical Society of Japan., No. 10, Jan. 1, 1989 (Jan. 1, 1989), pp. 1757-1764, XP055251263, JP.
Toshihide Hasegawa et al: "Diphenolic 9,9-Diarylfluorene Trimers and Derivatives Possessing Flexible Alkylene Chain Spacers: Synthesis of the Monomers, Their Polymerization, and Properties of the Resulting Polymers", Macromolecules, vol. 43, No. 1, Jan. 12, 2010 (Jan. 12, 2010), pp. 131-136, XP055251841, US.
Yoshihisa Okamoto et al: "Novel vinyl ether thermosetting resins", Polymer, Jan. 1, 1993 (Jan. 1, 1993), pp. 691-695, XP055251276.
CAS reaction database (Jun. 28, 2001)—included in the Office Action for U.S. Appl. No. 14/780,760 dated Jan. 31, 2017.
Extended European search report for European Patent Application No. 14775291.9 dated Jul. 25, 2016.
International Search Report for International Application No. PCT/JP2014/059309 dated Jun. 24, 2014.
International Search Report for International Application No. PCT/JP2014/059311 dated Jun. 24, 2014.
Office Action for Korean Patent Application No. 10-2015-7030693 dated Oct. 14, 2016.

(56) References Cited

OTHER PUBLICATIONS

Office Action for U.S. Appl. No. 14/780,786 dated Aug. 11, 2016.
Office Action for U.S. Appl. No. 14/780,786 dated Feb. 2, 2017.
Partial supplementary European search report for European Patent Application No. 14773950.2 dated Mar. 9, 2016.
Partial supplementary European search report for European Patent Application No. 14775291.9 dated Mar. 24, 2016.
Felix et al., Achieving Small Dimensions with an Environmentally Friendly Solvent: Photoresist Development Using Supercritical $CO_2$, Proc. of SPIE, 2008, vol. 6923, pp. 69233L-1-69233L-11, Abstract, Fig. 6.
Felix et al., Acid-Labile, Chain-Scission Polymer Systems Used as Positive-Tone Photoresists Developable in Supercritical $CO_2$, Chem. Mater., 2008, 20(9), pp. 2932-2936, Abstract, Fig. 2-3, Scheme 1.
Office Action in Chinese Patent Application No. 201480018794.2, dated Apr. 25, 2016.
Extended European search report in European Patent Application No. 14774297.7, dated Mar. 14, 2016.
Office Action issued in Korean Patent Application No. 10-2015-7030995, dated May 4, 2017.
Office Action issued to KR Patent Application No. 10-2015-7030693, dated Jun. 20, 2017.
Office Action issued in U.S. Appl. No. 14/780,786, dated Aug. 3, 2017.
Notification of Reasons for Refusal issued in JP Patent Application No. 2015-508792, dated Mar. 13, 2018.

\* cited by examiner

COMPOUND CONTAINING STRUCTURAL UNIT DERIVED FROM VINYL ETHER COMPOUND

This application is the U.S. National Phase under 35 U.S.C. § 371 of International Application PCT/JP2014/059308, filed Mar. 28, 2014, designating the U.S., and published in Japanese as WO 2014/157674 on Oct. 2, 2014, which claims priority to Japanese Patent Application No. 2013-075397, filed Mar. 29, 2013, the entire contents of which are incorporated herein by reference.

TECHNICAL FIELD

The present invention relates to a compound containing a structural unit derived from a vinyl ether compound, a method for producing the same, a composition containing the compound containing the structural unit, an optical-element sealing agent comprising the composition, an optical element sealed with the optical-element sealing agent, and a molded product obtained by molding the compound containing the structural unit that is a polymer.

BACKGROUND ART

Fused polycyclic compounds have various excellent functions and thus have been used for various applications. For example, compounds having a fluorene skeleton (for example, 9,9-bisphenylfluorene skeleton) that are fused polycyclic aromatic compounds are known to have excellent functions in terms of optical properties such as light transmittance and refractive index and thermal properties such as heat resistance. Therefore, compounds having a fluorene skeleton are used as raw materials for optical members such as lenses, prisms, filters, image display materials, optical disk substrates, optical fibers, optical waveguides, casing materials, films, and coating materials. Such compounds having a fluorene skeleton include, for example, compounds disclosed in Patent Literature 1.

Patent Document 1: Japanese Unexamined Patent Application, Publication No. 2011-201791

DISCLOSURE OF THE INVENTION

Problems to be Solved by the Invention

An object of the present invention is to provide a compound containing a structural unit derived from a novel vinyl ether compound, a method for producing the same, a composition containing the compound containing the structural unit, an optical-element sealing agent comprising the composition, an optical element sealed with the optical-element sealing agent, and a molded product obtained by molding the compound containing the structural unit that is a polymer.

Means for Solving the Problems

The present inventors have made extensive and intensive studies with a view to solving the above problems. As a result, the present inventors have found compounds containing a structural unit derived from a novel vinyl ether compound, which has led to the completion of the present invention. Specifically, the present invention provides the following.

According to a first aspect of the present invention, there is provided a compound containing a structural unit represented by the following general formula (1):

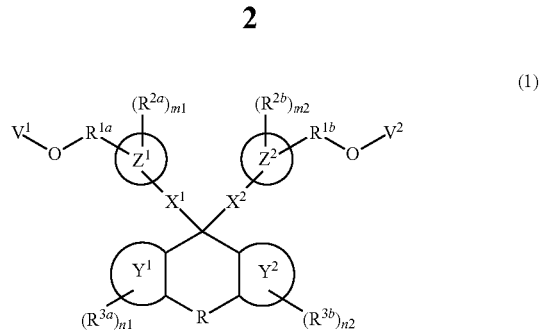

(wherein a ring $Z^1$ and a ring $Z^2$, which may be the same or different, represent an aromatic hydrocarbon ring; a ring $Y^1$ and a ring $Y^2$, which may be the same or different, represent an aromatic hydrocarbon ring; $X^1$ and $X^2$ each independently represent a single bond or a group represented by —S—; R represents a single bond, an optionally substituted methylene group, an ethylene group that is optionally substituted and may contain a hetero atom between two carbon atoms, a group represented by —O—, a group represented by —NH—, or a group represented by —S—; $R^{1a}$ and $R^{1b}$ each independently represent a single bond or an alkylene group having 1 to 4 carbon atoms; $R^{2a}$ and $R^{2b}$ each independently represent a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a sulfo group, or a group formed by substituting at least a part of hydrogen atoms bonded to carbon atoms contained in a monovalent hydrocarbon group, a group represented by —$OR^{4a}$, a group represented by —$SR^{4b}$, an acyl group, an alkoxycarbonyl group, a group represented by —$NHR^{4c}$, or a group represented by —$N(R^{4d})_2$ with a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a mesyloxy group, or a sulfo group; $R^{3a}$ and $R^{3b}$ each independently represent a cyano group, a halogen atom, or a monovalent hydrocarbon group; $R^{4a}$ to $R^{4d}$ each independently represent a monovalent hydrocarbon group; m1 and m2 each independently represent an integer of 0 or more; n1 and n2 each independently represent an integer of 0 to 4; $V^1$ represents a group represented by any of the following formulae (a1) to (a3); and $V^2$ represents a group represented by any of the following formulae (a1) to (a4))

-continued

(a4)

(wherein, in the formulae (a1) to (a4), *, , and * represent a bonding hand, provided that  represents a bonding hand with an oxygen atom connected directly to $V^1$ or $V^2$ in the general formula (1), and * represents a bonding hand with an oxygen atom connected directly to $V^2$ in the general formula (1).)

According to a second aspect of the present invention, there is provided a method for producing the above compound, the method comprising reacting a vinyl ether compound represented by the following general formula (4) with a hydroxyl-group-containing compound or an epoxy-group-containing compound:

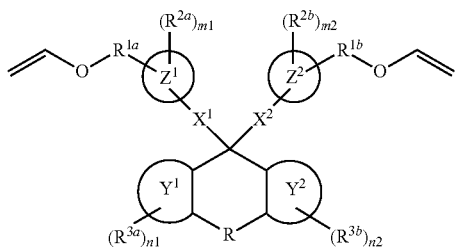
(4)

(wherein a ring $Z^1$, a ring $Z^2$, a ring $Y^1$, a ring $Y^2$, $X^2$, R, $R^{1a}$, $R^{1b}$, $R^{2a}$, $R^{2b}$, $R^{3a}$, $R^{3b}$, m1, m2, n1, and n2 are as defined above.)

According to a third aspect of the present invention, there is provided a composition comprising the above compound and a solvent.

According to a fourth aspect of the present invention, there is provided an optical-element sealing agent comprising the above composition.

According to a fifth aspect of the present invention, there is provided an optical element sealed with the above optical-element sealing agent.

According to a sixth aspect of the present invention, there is provided a molded product produced by molding the above compound that is a polymer comprising a structural unit represented by the general formula (1).

Effects of the Invention

The present invention can provide a compound containing a structural unit derived from a novel vinyl ether compound, a method for producing the same, a composition containing the compound containing the structural unit, an optical-element sealing agent comprising the composition, an optical element sealed with the optical-element sealing agent, and a molded product obtained by molding the compound containing the structural unit that is a polymer.

PREFERRED MODE FOR CARRYING OUT THE INVENTION

Compound Comprising a Structural Unit Represented by General Formula (1)

The compound according to the present invention comprises a structural unit represented by the general formula (1). Specifically, the compound according to the present invention comprises a structural unit derived from a vinyl ether compound.

Vinyl ether-based compounds having an alicyclic skeleton are less likely to pose problems related to working and environment such as skin irritation and odor and have excellent storage stability and dimensional stability and, thus, have been studied for use as transparent resins, adhesives, coating agents, and photoresist resins. For example, Japanese Unexamined Patent Application Publication No. 2007-231227 discloses a vinyl ether copolymer of 8-vinyloxytricyclo[5.2.1.0$^{2,6}$]decane with n-butyl vinyl ether, and this copolymer has been contemplated to be used in electric and electronic materials and optical material resins. According to studies conducted by the present inventors, however, vinyl ether-based compounds having an alicyclic skeleton have a problem of low heat resistance.

On the other hand, the compounds according to the present invention comprise a structural unit derived from novel vinyl ether compounds such as fluorene-based vinyl ether compounds. The compounds according to the present invention have excellent optical properties and at the same time high heat resistance and, thus, are suitable for use in transparent resins, adhesives, coating agents, and photoresist resins. In addition to the above applications, the compounds comprising a structural unit represented by the general formula (1) can be used in various applications, for example, alignment films and flattening films (for example, alignment films and flattening films used in liquid crystal displays and organic EL displays and the like; resist underlying films such as antireflection films, interlayer insulating films, and carbon hard masks; spacers and partition walls such as liquid crystal displays and organic EL displays; pixels and black matrixes in color filters of liquid crystal displays; display devices such as liquid crystal displays and organic EL displays; lenses (for example, microlenses), optical members such as optical fibers, light waveguides, prism sheets, holograms, high refractive index films, and retroreflection films; low moisture permeable membranes (for example, low moisture permeable membranes used as water vapor barrier layers; optical materials; and semiconductor materials.

In the general formula (1), examples of the ring $Z^1$ and the ring $Z^2$ include benzene rings, fused polycyclic aromatic hydrocarbon rings [for example, fused di- to tetracyclic aromatic hydrocarbon rings such as fused dicyclic hydrocarbon rings (for example, $C_{8-20}$ fused dicyclic hydrocarbon rings, preferably $C_{10-16}$ fused dicyclic hydrocarbon rings such as a naphthalene ring), and fused tricyclic aromatic hydrocarbon rings (for example, an anthracene ring, and a phenanthrene ring)]. The ring $Z^1$ and the ring $Z^2$ are preferably a benzene ring or a naphthalene ring, more preferably a naphthalene ring. The ring $Z^1$ and the ring $Z^2$ may be the same as or different from each other. For example, one of the rings may be a benzene ring with the other ring being a naphthalene ring or the like. Particularly preferably, both the rings are a naphthalene ring. The position of substitution of the ring $Z^1$ or the ring $Z^2$ bonded through $X^1$ or $X^2$ to carbon atoms to which both $X^1$ and $X^2$ are directly connected is not particularly limited. For example, when the ring $Z^1$ or the ring $Z^2$ is a naphthalene ring, the group corresponding to the ring $Z^1$ or the ring $Z^2$ bonded to the carbon atom may be, for example, a 1-naphthyl group or 2-naphthyl group.

In the general formula (1), examples of the ring $Y^1$ and the ring $Y^2$ include a benzene ring, fused polycyclic aromatic hydrocarbon rings [for example, fused di- to tetracyclic aromatic hydrocarbon rings such as fused dicyclic hydrocarbon rings (for example, $C_{8-20}$ fused dicyclic hydrocarbon rings, preferably $C_{10-16}$ fused dicyclic hydrocarbon rings, such as a naphthalene ring), and fused tricyclic aromatic hydrocarbon rings (for example, an anthracene ring and a phenanthrene ring)]. The ring $Y^1$ and the ring $Y^2$ are preferably a benzene ring or a naphthalene ring. The ring $Y^1$ and the ring $Y^2$ may be the same as or different from each other. For example, one of the rings may be a benzene ring with the other ring being a naphthalene ring or the like.

In the general formula (1), $X^1$ and $X^2$ each independently represent a single bond or a group represented by —S—; typically a single bond.

In the general formula (1), R represents a single bond, an optionally substituted methylene group, an ethylene group that is optionally substituted and may contain a hetero atom between two carbon atoms, a group represented by —O—, a group represented by —NH—, or a group represented by —S—; typically a single bond. Here, examples of substituents include a cyano group, halogen atoms (such as fluorine, chlorine, and bromine atoms), monovalent hydrocarbon groups [for example, alkyl groups ($C_{1-6}$ alkyl groups such as a methyl, ethyl, propyl, isopropyl, butyl, or t-butyl group), and aryl groups ($C_{6-10}$ aryl groups such as a phenyl group)]. Examples of hetero atoms include an oxygen atom, a nitrogen atom, a sulfur atom, or a silicon atom.

In the general formula (1), examples of $R^{1a}$ and $R^{1b}$ include a single bond; and alkylene groups having 1 to 4 carbon atoms such as methylene, ethylene, trimethylene, propylene, and butane-1,2-diyl groups. A single bond and $C_{2-4}$ alkylene groups (particularly $C_{2-3}$ alkylene groups such as ethylene and propylene groups) are preferred, and a single bond is more preferred. $R^{1a}$ and $R^{1b}$ may be the same as or different from each other.

In the general formula (1), examples of $R^{2a}$ and $R^{2b}$ include monovalent hydrocarbon groups such as alkyl groups (for example, $C_{1-12}$ alkyl groups such as methyl, ethyl, propyl, isopropyl, and butyl groups, preferably $C_{1-8}$ alkyl groups, more preferably $C_{1-6}$ alkyl groups), cycloalkyl groups (for example, $C_{5-10}$ cycloalkyl groups such as a cyclohexyl group, preferably $C_{5-8}$ cycloalkyl groups, more preferably $C_{5-6}$ cycloalkyl groups), aryl groups (for example, $C_{6-14}$ aryl groups such as phenyl, tolyl, xylyl, and naphthyl groups, preferably $C_{6-10}$ aryl groups, more preferably $C_{6-8}$ aryl groups), and aralkyl groups (for example, $C_{6-10}$ aryl $C_{1-4}$ alkyl groups such as benzyl and phenethyl groups); a hydroxyl group; groups represented by —$OR^{4a}$ wherein $R^{4a}$ represents a monovalent hydrocarbon group (for example, the above-exemplified monovalent hydrocarbon group) such as alkoxy groups (for example, $C_{1-12}$ alkoxy groups such as methoxy, ethoxy, propoxy, and butoxy groups, preferably $C_{1-8}$ alkoxy groups, more preferably $C_{1-6}$ alkoxy groups), cycloalkoxy groups ($C_{5-10}$ cycloalkoxy groups such as cyclohexyloxy groups), aryloxy groups ($C_{6-10}$ aryloxy groups such as phenoxy group), and aralkyloxy groups (for example, $C_{6-10}$ aryl $C_{1-4}$ alkyloxy groups such as a benzyloxy group); groups represented by —$SR^{4b}$ wherein $R^{4b}$ represents a monovalent hydrocarbon group (for example, the above-exemplified monovalent hydrocarbon group) such as alkylthio groups (for example, $C_{1-12}$ alkylthio groups such as methylthio, ethylthio, propylthio, and butylthio groups, preferably $C_{1-8}$ alkylthio groups, more preferably $C_{1-6}$ alkylthio groups), cycloalkylthio groups (for example, $C_{5-10}$ cycloalkylthio groups such as cyclohexylthio groups), aryl thio groups ($C_{6-10}$ aryl thio groups such as phenylthio), and aralkyl thio groups (for example, $C_{6-10}$ aryl $C_{1-4}$ alkylthio groups such as benzylthio groups); acyl groups ($C_{1-6}$ acyl groups such as an acetyl group); alkoxycarbonyl groups (for example, $C_{1-4}$ alkoxycarbonyl groups such as a methoxycarbonyl group); halogen atoms (for example, a fluorine atom, a chlorine atom, a bromine atom, and an iodine atom); a nitro group; a cyano group; a mercapto group; carboxyl group; an amino group; a carbamoyl group; groups represented by —$NHR^{4c}$ wherein $R^{4c}$ represents a monovalent hydrocarbon group (for example, the above-exemplified monovalent hydrocarbon group) such as alkylamino groups ($C_{1-12}$ alkylamino groups such as a methylamino group, an ethylamino group, a propylamino group, and a butylamino group, preferably $C_{1-8}$ alkylamino groups, more preferably $C_{1-6}$ alkylamino groups), cycloalkylamino groups (for example, $C_{5-10}$ cycloalkylamino groups such as a cyclohexylamino group), arylamino groups ($C_{6-10}$ aryl amino groups such as a phenylamino group), and aralkyl amino groups (for example, $C_{6-10}$ aryl $C_{1-4}$ alkylamino groups such as benzylamino group); groups represented by —$N(R^{4d})_2$ wherein $R^{4d}$ independently represents a monovalent hydrocarbon group (for example, the above-exemplified monovalent hydrocarbon group) such as dialkylamino groups (di($C_{1-12}$ alkyl)amino groups such as a dimethylamino group, a diethylamino group, a dipropylamino group, and a dibutylamino group, preferably di($C_{1-8}$ alkyl)amino groups, more preferably di($C_{1-6}$ alkyl)amino groups), dicycloalkylamino groups (di($C_{5-10}$ cycloalkyl) amino groups such as a dicyclohexylamino group), diaryl amino groups (di($C_{6-10}$ aryl)amino groups such as diphenylamino group), and diaralkyl amino groups (for example, di($C_{6-10}$ aryl $C_{1-4}$ alkyl)amino groups such as a dibenzylamino group); (meth)acryloyloxy groups; a sulfo group; and the above monovalent hydrocarbon groups, groups represented by —$OR^{4a}$, groups represented by —$SR^{4b}$, acyl groups, alkoxycarbonyl groups, groups represented by —$NHR^{4c}$, or groups obtained by substituting at least a part of hydrogen atoms bonded to carbon atoms contained in groups represented by —$N(R^{4d})_2$ with the above monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth) acryloyloxy group, a mesyloxy group, or group substituted by a sulfo group [for example, alkoxyaryl groups (for example, $C_{1-4}$ alkoxy $C_{6-10}$ aryl groups such as a methoxyphenyl group), alkoxycarbonylaryl groups (for example, $C_{1-4}$ alkoxycarbonyl $C_{6-10}$ aryl groups such as a methoxycarbonylphenyl group and an ethoxycarbonylphenyl)].

Among them, typical examples of $R^{2a}$ and $R^{2b}$ include monovalent hydrocarbon groups, groups represented by —$OR^{4a}$, groups represented by —$SR^{4b}$, acyl groups, alkoxycarbonyl groups, halogen atoms, nitro groups, cyano groups, groups represented by —$NHR^{4c}$, and groups represented by —$N(R^{4d})_2$.

Examples of preferred $R^{2a}$ and $R^{2b}$ include monovalent hydrocarbon groups [for example, alkyl groups (for example, $C_{1-6}$ alkyl groups), cycloalkyl groups (for example, $C_{5-8}$ cycloalkyl groups), aryl groups (for example, $C_{6-10}$ aryl groups), aralkyl groups (for example, $C_{6-8}$ aryl $C_{1-2}$ alkyl groups)], and alkoxy groups (for example, $C_{1-4}$ alkoxy groups). In particular, preferably, $R^{2a}$ and $R^{2b}$ represent a monovalent hydrocarbon group such as an alkyl group [for example, a $C_{1-4}$ alkyl group (particularly a methyl group)], an aryl group [for example, a $C_{6-10}$ aryl group (particularly a phenyl group)] (particularly an alkyl group).

When m1 is an integer of 2 or more, $R^{2a}$s may be different from or the same as each other. When m2 is an integer of 2 or more, $R^{2b}$s may be different from or the same as each other. Further, $R^{2a}$ and $R^{2b}$ may be the same as or different from each other.

In the general formula (1),
the number of $R^{2a}$s, that is, m1, may be selected according to the type of the ring $Z^1$ and may be, for example, 0 to 4, preferably 0 to 3, more preferably 0 to 2. Further, in the general formula (1), the number of groups $R^{2b}$s, that is, m2, may be selected according to the type of the ring $Z^2$ and may be, for example, 0 to 4, preferably 0 to 3, more preferably 0 to 2, m1 and m2 may be the same as or different from each other.

In the general formula (1), general examples of $R^{3a}$ and $R^{3b}$ include nonreactive substituents, for example, cyano groups, halogen atoms (for example, a fluorine atom, chlorine atom, and bromine atom), monovalent hydrocarbon groups [for example, alkyl groups and aryl groups ($C_{6-10}$ aryl groups such as phenyl group)]. A cyano group or an alkyl group is preferred, and an alkyl group is particularly preferred. Examples of alkyl groups include $C_{1-6}$ alkyl groups (for example, $C_{1-4}$ alkyl groups, particularly methyl groups) such as methyl, ethyl, propyl, isopropyl, butyl, and t-butyl groups. When n1 is an integer of 2 or more, $R^{3a}$s may be the same as or different from each other. When n2 is an integer of 2 or more, $R^{3b}$s may be the same as or different from each other. Further, $R^{3a}$ and $R^{3b}$ may be the same as or different from each other. The position of bonding of $R^{3a}$ and $R^{3b}$ to the ring $Y^1$ and the ring $Y^2$ (position of substitution) is not particularly limited. The number of substituents n1 and n2 is preferably 0 (zero) or 1, particularly preferably 0 (zero). n1 and n2 may be the same as or different from each other.

In the general formula (1), $V^1$ represents a group represented by any of the formulae (a1) to (a3), and $V^2$ represents a group represented by the formulae (a1) to (a4). The combination of $V^1$ and $V^2$ is not particularly limited. Examples of the combination include a combination of $V^1$ and $V^2$ wherein both $V^1$ and $V^2$ represent a group represented by the formula (a1), a combination of $V^1$ and $V^2$ wherein $V^1$ represents a group represented by the formula (a1) while $V^2$ represents a group represented by the formula (a4), a combination of $V^1$ and $V^2$ wherein both $V^1$ and $V^2$ represent a group represented by the formula (a2), a combination of $V^1$ and $V^2$ wherein $V^1$ represents a group represented by the formula (a2) while $V^2$ represents a group represented by the formula (a4), a combination of $V^1$ and $V^2$ wherein both $V^1$ and $V^2$ represent a group represented by the formula (a3), and a combination of $V^1$ and $V^2$ wherein $V^1$ represents a group represented by the formula (a3) while $V^2$ represents a group represented by the formula (a4).

In the formulae (a1) to (a4), *, , and * represent a bonding hand, provided that  represents a bonding hand with an oxygen atom connected directly to $V^1$ or $V^2$ in the general formula (1), and * represents a bonding hand with an oxygen atom connected directly to $V^2$ in the general formula (1). Examples of groups bonded to the structural unit represented by the general formula (1) through a bonding hand indicated by * include a group represented by —$CH_2$—, a group represented by —$CH(CH_3)$—, or a group represented by —O—.

A specific example of the structural unit represented by the general formula (1) is the structural unit represented by any of the following general formulae (b1) to (b6). In the structural unit represented by the following general formula (b1) or (b2), the bonding hand occurs at the α position of the vinyloxy group in the vinyl ether compound represented by the general formula (4) that will be described later (that is, the position of a carbon atom adjacent to an oxygen atom in the vinyloxy group). In the structural unit represented by the following general formula (b3) or (b4), the bonding hand occurs at the β position of the vinyloxy group in the vinyl ether compound (that is, the position of a carbon atom adjacent to a carbon atom at the α position). In the structural unit represented by the following general formula (b5) or (b6), the bonding hand occurs at the α position and the β position of the vinyloxy group in the vinyl ether compound.

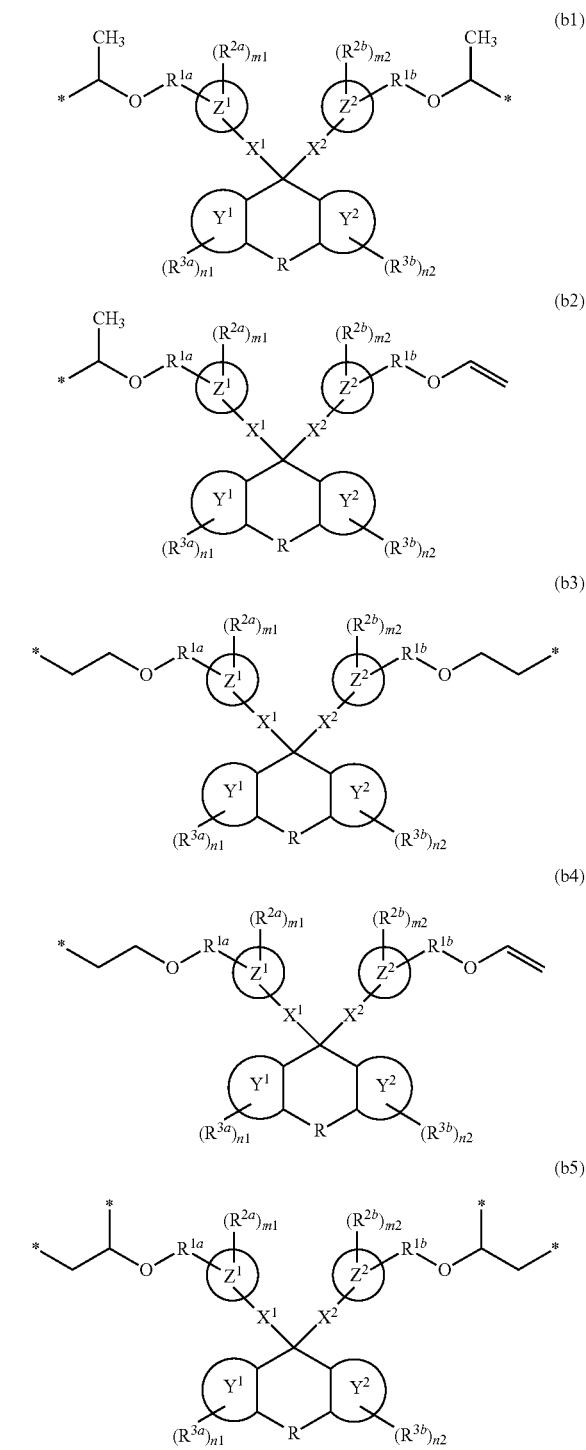

-continued

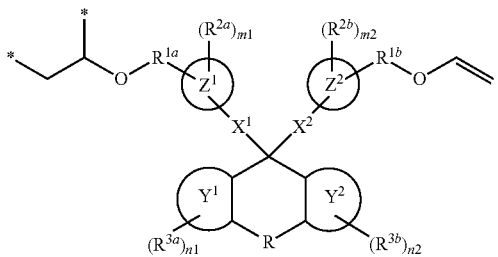

(b6)

(in the general formulae (b1) to (b6), a ring $Z^1$, a ring $Z^2$, a ring $Y^1$, a ring $Y^2$, $X^1$, $X^2$, R, $R^{1a}$, $R^{1b}$, $R^{2a}$, $R^{2b}$, $R^{3a}$, $R^{3b}$, m1, m2, n1, n2, and * are as defined above.)

In the compound containing the structural unit represented by the general formula (1), the number of structural units may be one or two or more. When the number of structural units is two or more, at least a part of the structural units may form a repeating unit. The structural unit that forms the repeating unit may solely form the repeating unit, or alternatively may form the repeating unit together with other structural units. That is, in compounds containing the structural unit, a plurality of the structural units per se may be repeated, or alternatively, a plurality of combinations of the structural unit with other structural units may be repeated.

Examples of compounds comprising the structural unit represented by the general formula (1) include polymers comprising the structural unit represented by the general formula (1). This polymer may contain, as the structural unit, only structural units represented by the general formula (1) or alternatively may further contain other structural units. The content of the structural unit represented by the general formula (1) in the polymer is preferably 30 to 100% by mole, more preferably 50 to 100% by mole, relative to all the structural units of the polymer, from the viewpoints of the refractive index, the light transmittance, and the heat resistance of the resultant cured film.

As will be described in the section of the production method of the compound according to the present invention, the structural unit represented by the general formula (1) is derived from the vinyl ether compound represented by the general formula (4) that will be described later, and the vinyl ether compound functions as cationically polymerizable monomers. A copolymer of the vinyl ether compound with another cationically polymerizable monomer may be mentioned as an example of the polymer comprising the structural unit represented by the general formula (1) and another structural unit.

Other cationically polymerizable monomers include, for example, organic compounds that, when exposed to light in the presence of a photoacid generating agent, cause a polymerization reaction or a crosslinking reaction. Specific examples thereof include epoxy compounds, oxetane compounds, oxolane compounds, cyclic acetal compounds, cyclic lactone compounds, thiirane compounds, thietane compounds, vinyl ether compounds other than the above vinyl ether compound, spiro ortho ester compounds that are reaction products between the epoxy compound and lactone, ethylenically unsaturated compounds, cyclic ether compounds, cyclic thio ether compounds, and vinyl compounds. Other cationically polymerizable monomers may be used solely or in a combination of two or more thereof.

Further, examples of polymers comprising the structural unit represented by the general formula (1) and other structural units include polymers comprising the structural unit represented by the following general formula (2).

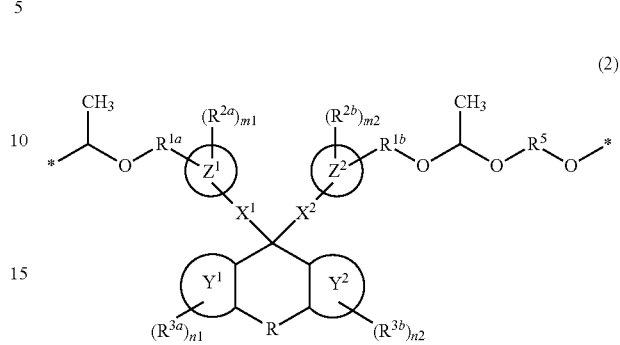

(2)

In the general formula (2), the ring $Z^1$, the ring $Z^2$, the ring $Y^1$, the ring $Y^2$, $X^1$, $X^2$, R, $R^{1a}$, $R^{1b}$, $R^{2a}$, $R^{2b}$, $R^{3a}$, $R^{3b}$, m1, m2, n1, n2, and * are as defined above; and $R^5$ represents an organic group.

In the general formula (2), $R^5$ represents, for example, a divalent hydrocarbon group, a divalent heterocyclic group, and a group formed by mutually bonding these groups, a group formed by mutually bonding any of these groups and a carbonyl group. A group formed by mutually bonding a divalent hydrocarbon group and a divalent hydrocarbon group and a carbonyl group (for example, a group formed by bonding a carbonyl group and a divalent hydrocarbon group and a carbonyl group in that order) is preferred. The divalent hydrocarbon group and the divalent heterocyclic group may have a substituent. Preferably, $R^5$ has a cyclic structure.

Examples of divalent hydrocarbon groups include divalent aliphatic hydrocarbon groups, divalent alicyclic hydrocarbon groups, divalent aromatic hydrocarbon groups, and groups formed by bonding two or more of these groups.

Divalent aliphatic hydrocarbon groups include, for example, alkylene groups having 1 to 20 carbon atoms, preferably 1 to 10 carbon atoms, still preferably 1 to 3 carbon atoms such as methylene, ethylene, propylene, isopropylene, butylene, isobutylene, s-butylene, t-butylene, ntylene, hexylene, decylene, and dodecylene groups; and alkenylene groups having 2 to 20 carbon atoms, preferably 2 to 10 carbon atoms, further preferably 2 or 3 carbon atoms such as vinylene, propenylene, and 1-butenylene groups; and alkynylene groups having 2 to 20 carbon atoms, preferably 2 to 10 carbon atoms, further preferably 2 or 3 carbon atoms, such as ethynylne and propynylene groups.

Divalent alicyclic hydrocarbon groups include cycloalkylene groups having 3 to 20 carbon atoms, preferably 3 to 15 carbon atoms, still preferably 5 to 8 carbon atoms, such as cyclopropylene, cyclobutylene, cyclopentylene, cyclohexylene, and cyclooctylene groups; cycloalkenylene groups having 3 to 20 carbon atoms, preferably 3 to 15 carbon atoms, still preferably 5 to 8 carbon atoms such as cyclopentenylene and cyclohexenylene groups; and divalent crosslinking cyclic hydrocarbon groups having 4 to 20 carbon atoms, preferably 6 to 16 carbon atoms, still preferably 7 to 12 carbon atoms such as perhydronaphtylene, norbornylene, adamantylene, and tetracyclo[$4.4.0.1^{2,5}.1^{7,10}$] dodecylene groups.

Divalent aromatic hydrocarbon groups include arylene groups having 6 to 20 carbon atoms, preferably 6 to 13 carbon atoms, such as phenylene, naphthylene, and fluorenylene groups.

Examples of groups formed by bonding a divalent aliphatic hydrocarbon group and a divalent alicyclic hydrocarbon group include cycloalkylene-alkylene groups (for example, $C_{3-20}$ cycloalkylene-$C_{1-4}$ alkylene groups) such as cyclopentylene methylene, cyclohexylene methylene, and cyclohexylene ethylene groups.

Examples of groups formed by bonding a divalent aliphatic hydrocarbon group and a divalent aromatic hydrocarbon group include arylene-alkylene groups (for example, $C_{6-20}$ arylene-$C_{1-4}$ alkylene groups), and arylene-alkylene-arylene groups (for example, $C_{6-20}$ arylene-$C_{1-4}$ alkylene group-$C_{6-20}$ arylene groups).

Examples of groups formed by bonding two or more divalent aromatic hydrocarbon groups include arylene-arylene groups (for example, $C_{6-20}$ arylene-$C_{6-20}$ arylene groups), arylene-arylene-arylene groups (for example, $C_{6-10}$ arylene-$C_{6-13}$ arylene-$C_{6-10}$ arylene groups).

Among these divalent hydrocarbon groups, those having a cyclic structure are preferred, and $C_{6-10}$ arylene-$C_{6-13}$ arylene group-$C_{6-10}$ arylene groups, $C_{6-20}$ arylene-$C_{1-4}$ alkylene group-$C_{6-20}$ arylene groups, and divalent crosslinking cyclic hydrocarbon groups having 7 to 12 carbon atoms are particularly preferred.

The divalent hydrocarbon groups may have various substituents, for example, halogen atoms, an oxo group, a hydroxyl group, substituted oxy groups (for example, alkoxy, aryloxy, aralkyloxy, and acyloxy groups), a carboxyl group, substituted oxycarbonyl groups (alkoxycarbonyl groups, aryloxycarbonyl groups, and aralkyloxycarbonyl groups), substituted or unsubstituted carbamoyl groups, a cyano group, a nitro group, substituted or unsubstituted amino groups, a sulfo group, and hetrocyclic groups. The hydroxyl group and the carboxyl group may be protected with protective groups commonly used in the field of organic synthesis. An aromatic or non-aromatic hetero ring may be fused to the divalent alicyclic hydrocarbon group and the ring of the divalent aromatic hydrocarbon group.

The divalent heterocyclic group is a group formed by removing two hydrogen atoms from the heterocyclic compound. The heterocyclic compound may be an aromatic heterocyclic compound or a non-aromatic heterocyclic compound. Such heterocyclic compounds include, for example, heterocyclic compounds containing an oxygen atom as a hetero atom (for example, three-membered ring heterocyclic compounds such as oxirane, four-membered ring heterocyclic compounds such as oxetane, five-membered ring heterocyclic compounds such as furan, tetrahydrofuran, oxazole, and γ-butyrolactone, six-membered ring heterocyclic compounds such as 4-oxo-4H-pyran, tetrahydropyran, and morpholine, heterocyclic compounds having a fused ring such as benzofuran, 4-oxo-4H-chromene, and chromane, and heterocyclic compounds having a crosslinking ring such as 3-oxatricyclo[4.3.1.1$^{4,8}$]undecane-2-one, 3-oxatricyclo[4.2.1.0$^{4,8}$]nonan-2-one), heterocyclic compounds containing a sulfur atom as a hetero atom (for example, five-membered ring heterocyclic compounds such as thiophene, thiazole, and thiadiazole, six-membered ring heterocyclic compounds such as 4-oxo-4H-thiopyran, and heterocyclic compounds having a fused ring such as benzothiophene), heterocyclic compounds containing a nitrogen atom as a hetero atom (for example, five-membered ring heterocyclic compounds such as pyrrole, pyrrolidine, pyrazole, imidazole, and triazole, six-membered ring heterocyclic compounds such as pyridine, pyridazine, pyrimidine, pyrazine, piperidine, and piperazine, and heterocyclic compounds having a fused ring such as indole, indoline, quinoline, acridine, naphthyridine, quinazoline, and purine).

The divalent heterocyclic group may have, in addition to substituents optionally possessed by the divalent hydrocarbon group, alkyl groups (for example, $C_{1-4}$ alkyl groups such as a methyl group and an ethyl group), a cycloalkyl group, an aryl group (for example, $C_{6-10}$ aryl groups such as phenyl and naphthyl groups).

The mass average molecular weight of the polymer containing a structural unit represented by the general formula (1) is not particularly limited but is preferably not more than 300,000, more preferably 2,000 to 100,000. The term "mass average molecular weight" as used herein refers to a mass average molecular weight in terms of standard polystyrene as measured by gel permeation chromatography (GPC).

The degree of polymerization of the polymer containing a structural unit represented by the general formula (1) is not particularly limited and may be, for example, 2 to 600. The polymer containing the structural unit represented by the general formula (1) may be an oligomer compound having a degree of polymerization of 2 to 10.

Polymers represented by any one of the general formulae (c1) to (c3) may be mentioned as specific examples of the polymer containing a structural unit represented by the general formula (1). Polymers represented by the general formula (c1) are linear polymers obtained by forming a new bond between carbon atoms at the α position of the vinyloxy group as a result of a reaction between vinyl ether compounds represented by the general formula (4). Polymers represented by the following general formula (c2) are comb-like polymers obtained by forming a new bond between the α position and the β position of the vinyloxy group as a result of a reaction between vinyl ether compounds. Polymers represented by the following general formula (c3) are polymers obtained by a reaction of the vinyl ether compound with another compound containing a group $R^5$ at the α position of the vinyloxy group. Among them, polymers represented by the following general formula (c1) and polymers represented by the following general formula (c3) are preferred. From the viewpoints of solubility and the like, polymers represented by the following general formula (c1) are preferably oligomer compounds wherein i is 2 to 10.

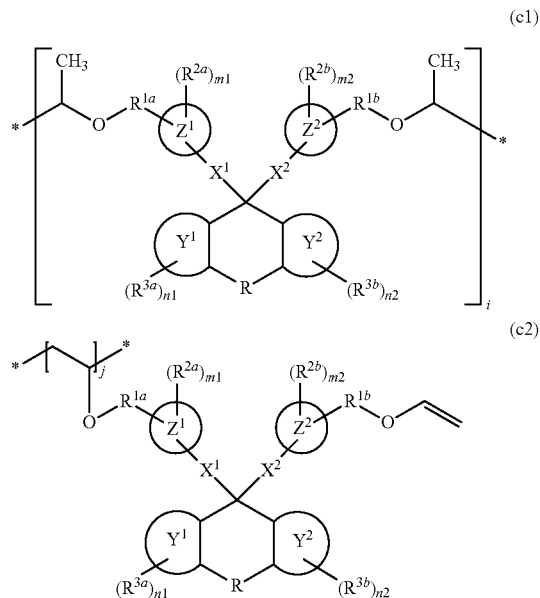

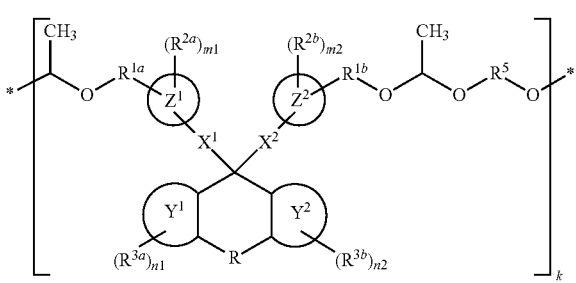

(c3)

In the above formula, a ring $Z^1$, a ring $Z^2$, a ring $Y^1$, a ring $Y^2$, $X^1$, $X^2$, R, $R^{1a}$, $R^{1b}$, $R^{2a}$, $R^{2b}$, $R^{3a}$, $R^{3b}$, $R^5$, m1, m2, n1, n2, and * are as defined above and i, j, and k are a number from 2 to 600.

Further, additional compounds containing a structural unit represented by the general formula (1) include, for example, compounds represented by the following general formula (3).

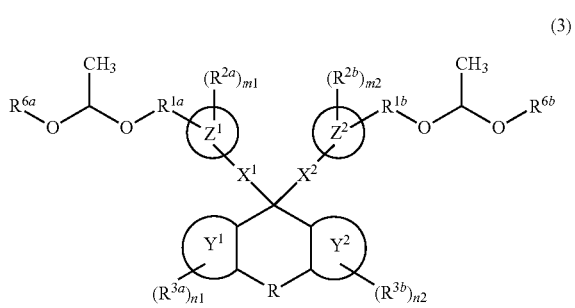

(3)

In the general formula (3), a ring $Z^1$, a ring $Z^2$, a ring $Y^1$, a ring $Y^2$, $X^1$, $X^2$, R, $R^{1a}$, $R^{1b}$, $R^{2a}$, $R^{2b}$, $R^{3a}$, $R^{3b}$, m1, m2, n1, and n2 are as defined above and $R^{6a}$ and $R^{6b}$ each independently represent an organic group.

In the general formula (3), examples of $R^{6a}$ and $R^{6b}$ include monovalent hydrocarbon groups, monovalent heterocyclic groups, groups formed by mutual bonding between those two groups, and groups formed by mutual bonding between any of these groups and a carbonyl group, and monovalent hydrocarbon groups and groups formed by mutual bonding between the monovalent hydrocarbon group and the carbonyl group are preferred. Monovalent hydrocarbon groups and monovalent heterocyclic groups may have a substituent. Preferably, $R^{6a}$ and $R^{6b}$ have a cyclic structure.

Examples of monovalent hydrocarbon groups include monovalent aliphatic hydrocarbon groups, monovalent alicyclic hydrocarbon groups, monovalent aromatic hydrocarbon groups, and groups formed by bonding between two or more of these groups.

Examples of monovalent aliphatic hydrocarbon groups include alkyl groups having 1 to 20 carbon atoms, preferably 1 to 10 carbon atoms, more preferably 1 to 3 carbon atoms, such as methyl groups, ethyl groups propyl groups, isopropyl groups, butyl groups, isobutyl groups, s-butyl groups, t-butyl groups, pentyl, hexyl, decyl, and dodecyl groups; alkenyl groups having 2 to 20 carbon atoms, preferably 2 to 10 carbon atoms, more preferably 2 or 3 carbon atoms, such as vinyl groups, aryl groups, and 1-butenyl groups; and alkynyl groups having 2 to 20 carbon atoms, preferably 2 to 10 carbon atoms, more preferably 2 or 3 carbon atoms, such as ethynyl and propynyl groups.

Monovalent alicyclic hydrocarbon groups include cycloalkyl groups having 3 to 20 carbon atoms, preferably 3 to 15 carbon atoms, more preferably 5 to 8 carbon atoms, such as cyclopropyl, cyclobutyl, cyclopentyl, cyclohexyl, and cyclooctyl groups; cycloalkenyl groups having 3 to 20 carbon atoms, preferably 3 to 15 carbon atoms, more preferably 5 to 8 carbon atoms, such as cyclopentenyl and cyclohexenyl groups; and monovalent crosslinking cyclic hydrocarbon groups having 4 to 20 carbon atoms, preferably 6 to 16 carbon atoms, more preferably 7 to 12 carbon atoms, such as perhydronaphthalen-1-yl, norbornyl, adamantyl, and tetracyclo[4.4.0.1$^{2,5}$.0.1$^{7,10}$]dodecan-3-yl groups.

Monovalent aromatic hydrocarbon groups include aryl groups having 6 to 20 carbon atoms, preferably 6 to 13 carbon atoms, such as phenyl, naphthyl, and fluorenyl groups.

Groups formed by bonding monovalent aliphatic hydrocarbon groups and monovalent alicyclic hydrocarbon groups include, for example, cycloalkyl-alkyl groups (for example, $C_{3-20}$ cycloalkyl-$C_{1-4}$alkyl groups) such as cyclopentylmethyl, cyclohexylmethyl, and 2-cyclohexylethyl groups.

Groups formed by bonding monovalent aliphatic hydrocarbon groups and monovalent aromatic hydrocarbon groups include, for example, aralkyl groups (for example, $C_{7-18}$ aralkyl groups), alkyl-aryl groups (for example, $C_{1-4}$ alkyl-$C_{6-20}$ aryl groups, more specifically a phenyl or naphthyl group substituted by 1 to 4 $C_{1-4}$ alkyl groups), aryl-alkyl-aryl groups (for example, a $C_{6-20}$ aryl-$C_{1-4}$ alkyl group-$C_{6-20}$ aryl group).

Groups formed by bonding between two or more monovalent aromatic hydrocarbon groups include, for example, aryl-aryl groups (for example, $C_{6-20}$ aryl-$C_{6-20}$ aryl groups), aryl-aryl-aryl groups (for example, $C_{6-10}$ aryl-$C_{6-13}$ aryl-$C_{6-10}$ aryl groups).

Among monovalent hydrocarbon groups, monovalent hydrocarbon groups having a cyclic structure are preferred, and $C_{6-10}$ aryl-$C_{6-13}$ aryl-$C_{6-10}$ aryl groups, $C_{6-20}$ aryl-$C_{1-4}$ alkyl group-$C_{6-20}$ aryl groups, and monovalent crosslinking cyclic hydrocarbon groups having 7 to 12 carbon atoms are particularly preferred.

The monovalent hydrocarbon group may have various substituents. Specific examples of the substituents include those described above as examples of substituents optionally possessed by divalent hydrocarbon groups. Further, aromatic or non-aromatic heterocyclic rings may be condensed with the ring of monovalent alicyclic hydrocarbon and monovalent aromatic hydrocarbon groups.

The monovalent heterocyclic group represents a group formed by removing one hydrogen atom from the heterocyclic compound. The heterocyclic compound may be an aromatic heterocyclic compound or a non-aromatic heterocyclic compound. Such heterocyclic rings include, for example, those exemplified above in the description in connection with divalent heterocyclic groups. The monovalent heterocyclic group may contain, in addition to substituents optionally possessed by the monovalent hydrocarbon groups, substituents such as alkyl groups (for example, $C_{1-4}$ alkyl groups such as methyl and ethyl groups), cycloalkyl groups, and aryl groups (for example, $C_{6-10}$ aryl groups such as phenyl and naphthyl groups).

Method for Producing Compounds Containing Structural Unit Represented by General Formula (1)

Compounds containing a structural unit represented by the general formula (1) may be produced by a reaction between vinyl ether compounds represented by the following general formula (4) or by a reaction between a vinyl ether compound represented by the following general formula (4) and another compound reactive with a vinyloxy group:

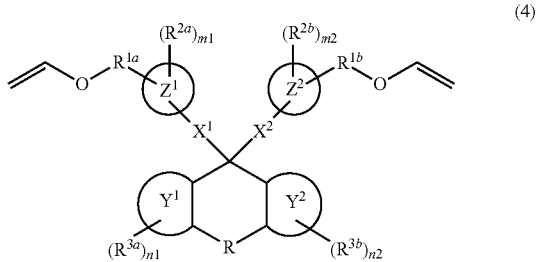

(wherein a ring $Z^1$, a ring $Z^2$, a ring $Y^1$, a ring $Y^2$, $X^1$, $X^2$, R, $R^{1a}$, $R^{1b}$, $R^{2a}$, $R^{2b}$, $R^{3a}$, $R^{3b}$, m1, m2, n1, and n2 are as defined above.)

Reaction Between Vinyl Ether Compounds Represented by the General Formula (4)

Polymers containing a structural unit represented by the general formula (1) can be obtained by a reaction between vinyl ether compounds represented by the general formula (4). The vinyl ether compound may be used solely or in a combination of two or more thereof.

The above reaction is carried out by conventional cation polymerization. Cation polymerization initiators usable in the cation polymerization may be commonly used cation polymerization initiators and include, for example, Lewis acids such as tin tetrabromide ($SnBr_4$) and boron trifluoride ($BF_3$) and protonic acids such as sulfuric acid. The cation polymerization initiator may be used solely or in a combination of two or more. The amount of the cation polymerization initiator used is preferably 0.01 to 10% by mole, more preferably 0.05 to 5 by mole, relative to the vinyl ether compound represented by the general formula (4).

The reaction is generally carried out in a solvent. Solvents include, but are not limited to, aliphatic hydrocarbon-based solvents such as hexane, aromatic hydrocarbon-based solvents such as toluene, and methylene chloride. The solvent may be used solely or in a combination of two or more thereof.

The reaction temperature may be, for example, −100 to 30° C., preferably −30 to 10° C. The reaction time may be, for example, 20 min to 10 hrs, preferably 30 min to 6 hrs.

Reaction Between Vinyl Ether Compound Represented by General Formula (4) and Another Compound Reactive with a Vinyloxy Group Polymers containing a structural unit represented by the general formula (1) can be obtained by a reaction between a vinyl ether compound represented by the general formula (4) and another compound reactive with a vinyloxy group. Each of the vinyl ether compound and the other compound reactive with a vinyloxy group may be used solely or in a combination of two or more thereof.

Other compounds reactive with the vinyloxy group include, for example, compounds containing a group reactive with a vinyloxy group such as a hydroxyl group, an epoxy group, a carboxyl group, a vinyloxy group, a thiol group, a phosphoric acid group (—O—PO(OH)$_2$), a phosphoric ester group (—O—PO(OH) (OR$^A$)), a sulfo group (—SO$_2$—OH), a sulfonic acid amide group (—SO$_2$—NR$^B$H), and a dicarboxylic acid imide group (—CO—NH—CO—) (that is, hydroxyl-group-containing compounds, epoxy-group-containing compounds, carboxyl-group-containing compounds, vinyloxy-group-containing compounds, thiol-group-containing compounds, phosphoric acid-containing compounds, phosphoric acid ester-group-containing compounds, sulfo-group-containing compounds, sulfonic acid amide group-containing compounds, and dicarboxylic acid imide-group-containing compounds), hydrogen cyanide, and hydrogen azide. $R^A$ represents a monovalent organic group; and $R^B$ represents a hydrogen atom or a monovalent organic group. The hydroxyl group, the carboxyl group, the vinyloxy group, the thiol group, the phosphoric acid group, the phosphoric acid ester group, the sulfo group, the sulfonic acid amide group, or the dicarboxylic acid imide group reacts with the vinyl ether compound at the α position of the vinyloxy group in the vinyl ether compound represented by the general formula (4). Hydrogen cyanide and hydrogen azide also react with the vinyl ether compound at the α position of the vinyloxy group in the vinyl ether compound. On the other hand, the epoxy group reacts with the vinyl ether compound at the α position and β position of the vinyloxy group in the vinyl ether compound.

In particular, polymers containing a structural unit represented by the general formula (2) or compounds represented by the general formula (3) can be obtained by reacting a vinyl ether compound represented by the general formula (4) with a hydroxyl-group-containing compound, an epoxy-group-containing compound, a carboxyl-group-containing compound, a phosphoric acid-group-containing compound, a phosphoric acid ester-group-containing compound, or a sulfo-group-containing compound.

The reaction between the vinyl ether compound represented by the general formula (4) and another compound reactive with the vinyloxy group is preferably carried out in the form of a solution. Solvents usable in the reaction may be conventional solvents. From the viewpoint of suppressing a side reaction with reaction products such as the vinyl ether compound and a catalyst that will be described later, for example, solvents free from reactivity with these substances are preferred. Specific examples of such solvents include tetrahydrofuran, cyclocyclohexanone, propylene glycol monomethyl ether acetate, hydrocarbon-based solvents (for example, aliphatic hydrocarbon-based solvents such as hexane, and aromatic hydrocarbon-based solvents such as toluene). The solvent may be used solely or in a combination of two or more thereof.

In the reaction, a catalyst may be used for reaction rate acceleration purposes. Acid catalysts are usually used as the catalyst. Acid catalysts include sulfuric acid, hydrochloric acid, p-toluenesulfonic acid, p-toluenesulfonic acid pyridium, and boron trifluoride. Among them, hydrochloric acid, p-toluenesulfonic acid, p-toluenesulfonic acid pyridium and the like are preferred. The amount of the catalyst used is 0.01 to 10% by mole, more preferably 0.05 to 5% by mole relative to the vinyl ether compound represented by the general formula (4). For example, when the acid catalyst is used in a pretreatment step and the liquid after the pretreatment is used in the reaction as is, there is no need to add the acid catalyst again.

Specifically, the reaction operation can be carried out, for example, by adding the vinyl ether compound represented by the general formula (4) and optionally a catalyst to a solution containing another compound reactive with the vinyloxy group at a predetermined reaction temperature. The addition may be carried out at a time or by split addition or continuous dropping. The reaction temperature may be, for example, 0 to 150° C., preferably 10 to 100° C. The reaction time may be, for example, 20 min to 10 hrs, preferably 30 min to 4 hrs.

The amount of the vinyl ether compound represented by the general formula (4) is preferably 0.01 to 1000% by mass, more preferably 200 to 800% by mass relative to the other compound reactive with the vinyloxy group. When the amount of vinyl ether compound used is not less than 0.01% by mass, the reaction easily proceeds and a polymeric film can easily be obtained when the reaction product is a polymer. When the amount of vinyl ether compound used is not less than 200% by mass, high-refractive-index cured films can easily be obtained from the obtained compound regardless of the type of the other compound reactive with the vinyloxy group. On the other hand, when the amount of vinyl ether compound used is not more than 1000% by mass, advantageously, the degree of dispersion of the molecular weight is narrow and high-refractive-index cured films that are even in plane can easily be obtained.

When the other compound reactive with the vinyloxy group is a vinyoxy-group-containing compound, reaction conditions are preferably those described above in connection with the reaction between the vinyl ether compounds represented by the general formula (4).

Vinyl Ether Compounds Represented by General Formula (4)

Among vinyl ether compounds represented by the general formula (4), specific examples of particularly preferred vinyl ether compounds include compounds represented by the following formulae.

-continued

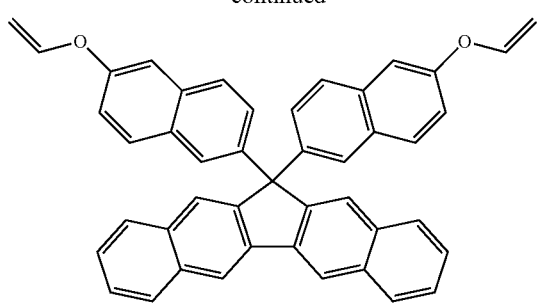

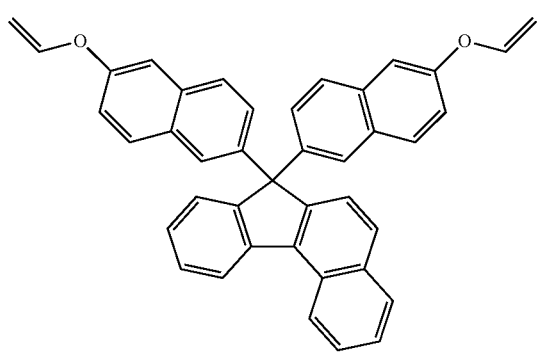

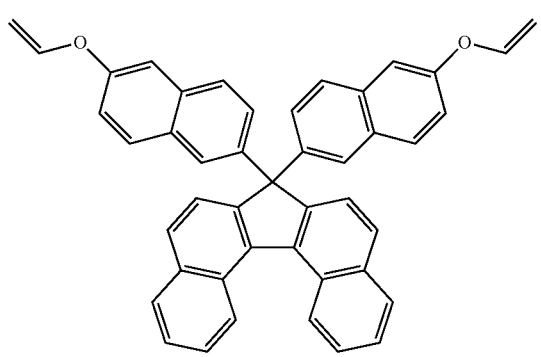

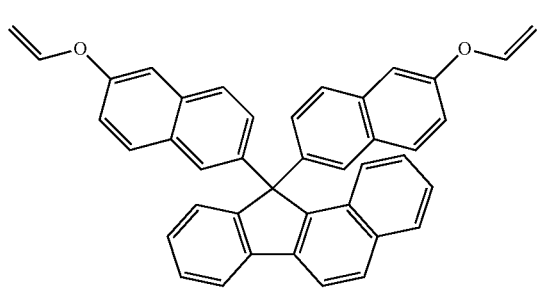

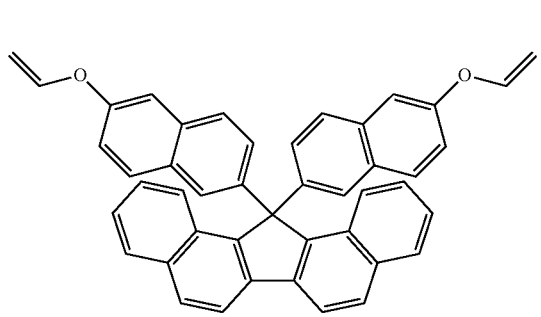

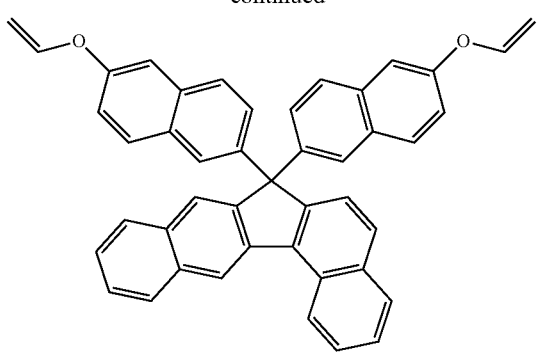
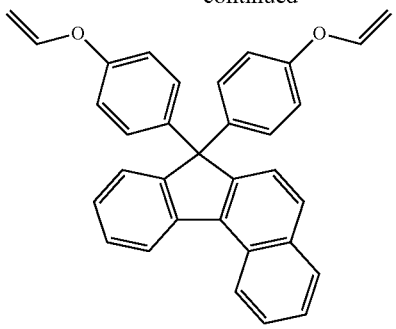
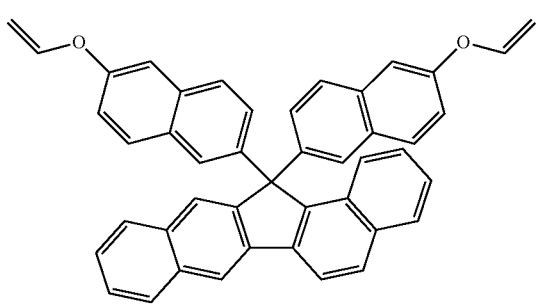
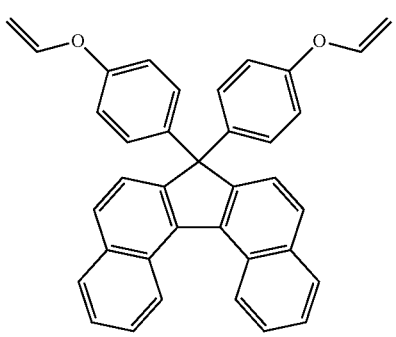
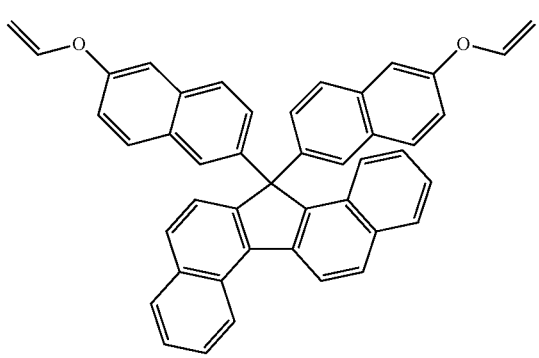
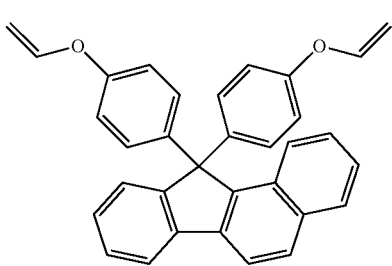
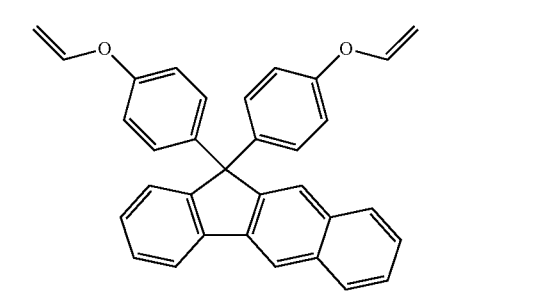
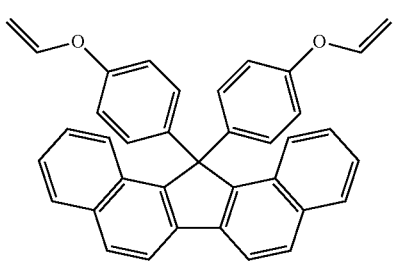
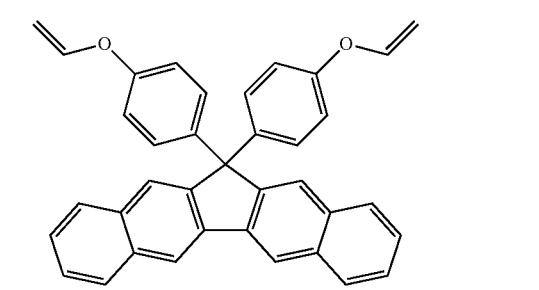
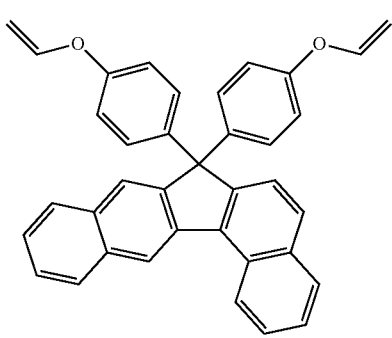

-continued

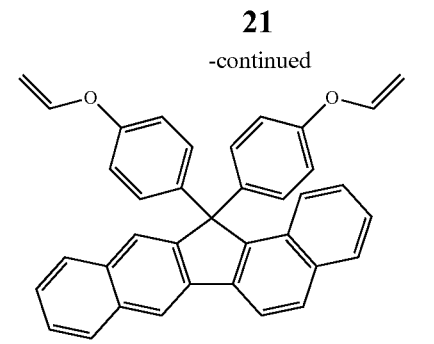

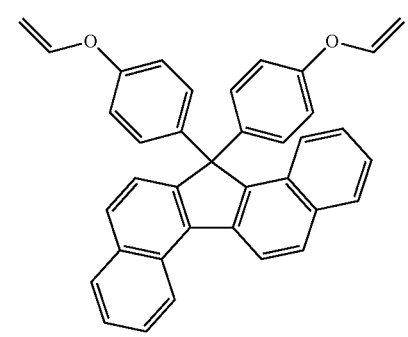

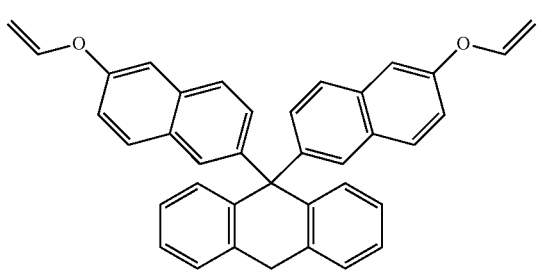

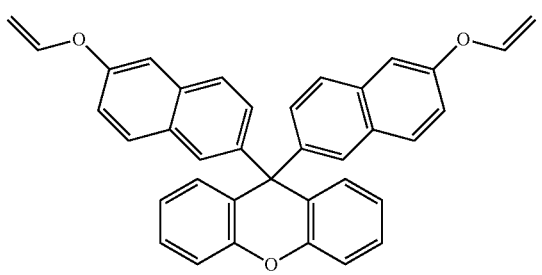

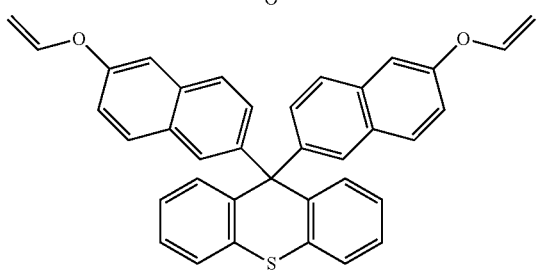

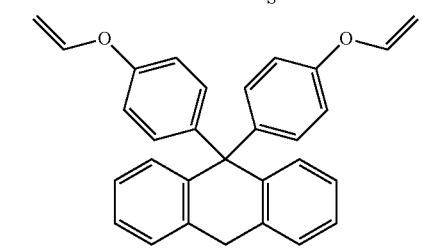

-continued

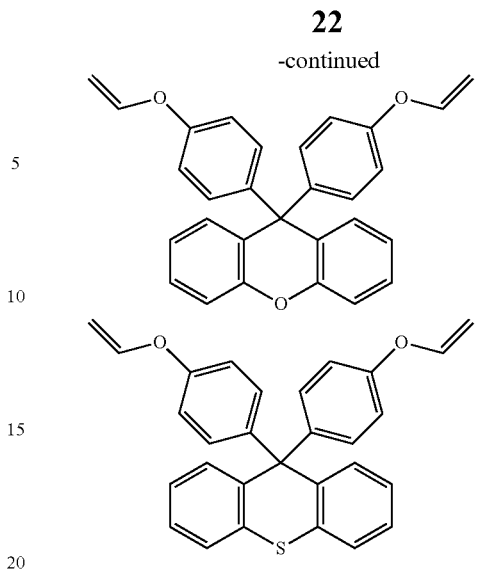

Vinyl ether compounds represented by the general formula (4) can be synthesized, for example, by reacting a vinyl ester compound represented by the following general formula (5) with a hydroxyl-group-containing compound represented by the following general formula (6) in the presence of a transition element compound catalyst and an inorganic base according to a production method described in Japanese Unexamined Patent Application, Publication No. 2008-266169. The inorganic base is preferably a solid inorganic base containing not less than 10% by weight of particles having a particle diameter of less than 150 μm. Specifically, vinyl ether compounds represented by the general formula (4) can be synthesized as described in Synthesis Examples 1 and 2 that will be described later.

$$R^7\text{—CO—O—CH}=\text{CH}_2 \quad (5)$$

(wherein $R^7$ represents a hydrogen atom or an organic group.)

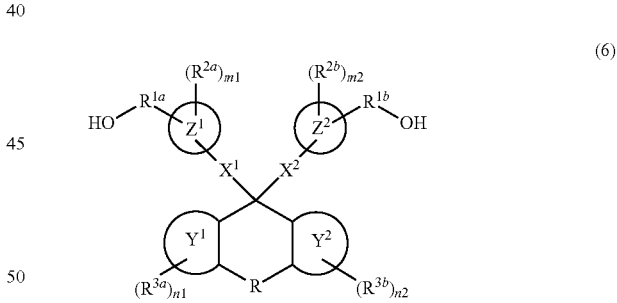

(6)

(wherein a ring $Z^1$, a ring $Z^2$, a ring $Y^1$, a ring $Y^2$, $X^1$, $X^2$, R, $R^{1a}$, $R^{1b}$, $R^{2a}$, $R^{2b}$, $R^{3a}$, $R^{3b}$, m1, m2, n1, and n2 are as defined above.)

Compounds represented by the general formula (6) are produced by the following method.

Among compounds represented by the general formula (6), compounds wherein $X^1$ and $X^2$ represent a single bond can be synthesized, for example, by reacting a compound represented by the following general formula (7-1) with a compound represented by the following general formula (8-1) and a compound represented by the following general formula (9) in the presence of an acid catalyst.

Among compounds represented by the general formula (6), compounds wherein $X^1$ represents a single bond and $X^2$ represents a group represented by —S— can be synthesized, for example, by reacting a compound represented by the general formula (7-1), a compound represented by the general formula (8-2), and a compound represented by the general formula (9) in the presence of an acid catalyst.

Among compounds represented by the general formula (6), compounds wherein $X^1$ represents a group represented by —S— and $X^2$ represents a single bond can be synthesized, for example, by reacting a compound represented by the general formula (7-2), a compound represented by the general formula (8-1), and a compound represented by the general formula (9) in the presence of an acid catalyst.

Among compounds represented by the general formula (6), compounds wherein $X^1$ and $X^2$ represent a group represented by —S— can be synthesized, for example, by reacting a compound represented by the general formula (7-2), a compound represented by the general formula (8-2), and a compound represented by the general formula (9) in the presence of an acid catalyst.

After the completion of the reaction, intended hydroxyl-group-containing compounds may be separated, for example, by conventional separation methods such as silica gel column chromatography.

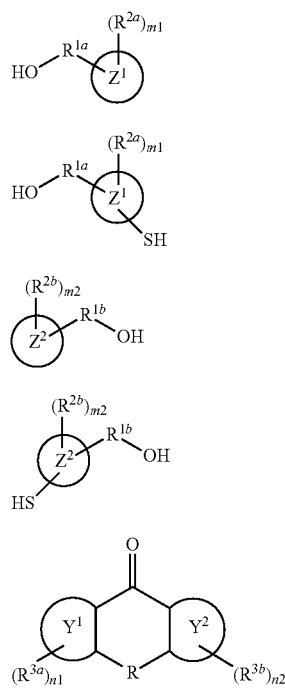

(wherein, in the general formulae (7-1), (7-2), (8-1), (8-2), and (9), a ring $Z^1$, a ring $Z^2$, a ring $Y^1$, ring $Y^2$, R, $R^{1a}$, $R^{1b}$, $R^{2a}$, $R^{2b}$, $R^{3a}$, $R^{3b}$, m1, m2, n1, and n2 are as defined above.)

Acid catalysts, reaction conditions and the like usable in the synthesis of compounds represented by the general formula (6) may be, for example, those described as usable in the production method of fluorene-based compounds described in the claims of Patent Literature 1 or Japanese Unexamined Patent Application, Publication No. 2002-255929.

Vinyl ether compounds represented by the general formula (4) may be purified after the completion of the synthesis. The purification method is not particularly limited, and conventional methods such as silica gel column chromatography may be used as the purification method. The purification can realize an improvement in purity of the vinyl ether compound represented by the general formula (4) and a reduction in the content of the metallic component. The purified vinyl ether compound has an improved reactivity and effectively suppresses coloring during the reaction.

The vinyl ether compound represented by the general formula (4) has a high reactivity by virtue of the presence of the vinyloxy group while maintaining excellent optical properties and thermal properties. In particular, when the ring $Y^1$ and the ring $Y^2$ represent a benzene ring and R represents a single bond, vinyl ether compounds represented by the general formula (4) have a fluorene skeleton and possess excellent optical properties and thermal properties. Such vinyl ether compounds represented by the general formula (4) can be cationically polymerized and thus function as cationically polymerizable monomers.

Other Compounds Reactive with Vinyloxy Groups

As described above, examples of other compounds reactive with the vinyloxy group include compounds containing a group reactive with the vinyloxy group, hydrogen cyanide and hydrogen azide. Compounds containing a group reactive with the vinyloxy group are not particularly limited as long as at least one group reactive with the vinyloxy group is present. Hydroxyl-group-containing compounds, epoxy-group-containing compounds, carboxyl-group-containing compounds, vinyloxy-group-containing compounds, and thiol-group-containing compounds will be described in more detail below.

[Hydroxyl-Group-Containing Compounds]

Hydroxyl-group-containing compounds are not particularly limited as long as at least one hydroxyl group is contained in the compound. Hydroxyl-group-containing compounds that react with vinyl ether compounds represented by the general formula (4) to form polymers containing a structural unit represented by the general formula (2) or compounds represented by the general formula (3) are preferred. Compounds that contain an organic group having a cyclic structure are more preferred.

When polymers containing a structural unit represented by the general formula (2) are produced, compounds represented by the following general formula, for example, may be mentioned as the hydroxyl-group-containing compound.

HO—$R^8$—OH (wherein $R^8$ is as defined above.)

Examples of $R^8$ include, among groups exemplified as $R^5$, divalent hydrocarbon groups, divalent heterocyclic groups, and groups formed by mutual bonding of these groups.

When compounds represented by the general formula (3) are produced, for example, compounds represented by the following general formula may be mentioned as the hydroxyl-group-containing compound.

$R^9$—OH (wherein $R^9$ represents an organic group.)

Examples of $R^9$ include, among groups exemplified as $R^{6a}$ and $R^{6b}$, monovalent hydrocarbon groups, monovalent heterocyclic groups, and groups formed by mutual bonding of these groups.

Specific examples of hydroxyl-group-containing compounds include a compound represented by the following formula.

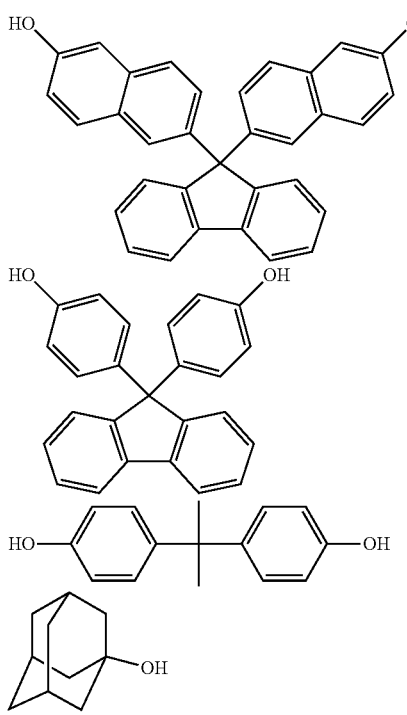

[Epoxy-Group-Containing Compounds]

Epoxy-group-containing compounds are not particularly limited as long as at least one epoxy group is contained in the compound. Epoxy-group-containing compounds are preferably those that can react with vinyl ether compounds represented by the general formula (4) to form polymers containing a structural unit represented by the general formula (2) or compounds represented by the general formula (3). Compounds that contain an organic group having a cyclic structure involved in the reaction with the vinyl ether compound in addition to an oxirane ring are more preferred.

When polymers containing a structural unit represented by the general formula (2) are produced, for example, compounds represented by the following general formula may be mentioned as the epoxy-group-containing compound.

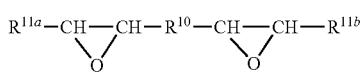

(wherein $R^{10}$ represents an organic group; and $R^{11a}$ and $R^{11b}$ each independently represent a hydrogen atom or an organic group.)

Examples of $R^{10}$ include, among groups exemplified as $R^5$, divalent hydrocarbon groups, divalent heterocyclic groups, and groups formed by mutual bonding of these groups. Examples of $R^{11a}$ and $R^{11b}$ that represent an organic group include, among groups exemplified as $R^{6a}$ or $R^{6b}$, for example, monovalent hydrocarbon groups, monovalent heterocyclic groups, and groups formed by mutual bonding of these groups, provided that at least two of $R^{10}$, $R^{11a}$, and $R^{11b}$ may be mutually bonded to form a ring. Examples of rings formed in this way include alicyclic hydrocarbon rings, aromatic hydrocarbon rings, heterocyclic rings, and rings formed by bonding and/or condensation of two or more of these rings.

When compounds represented by the general formula (3) are produced, examples of epoxy-group-containing compounds include, for example, compounds represented by the following general formula.

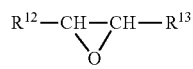

(wherein $R^{12}$ represents an organic group; and $R^{13}$ represents a hydrogen atom or an organic group.)

$R^{12}$ and $R^{13}$ that represents an organic group include, among groups exemplified as $R^{6a}$ or $R^{6b}$, for example, monovalent hydrocarbon groups, monovalent heterocyclic groups, and groups formed by mutual bonding of these groups, provided that $R^{12}$ and $R^{13}$ may be mutually bonded to form a ring. Examples of rings formed in this way include alicyclic hydrocarbon rings, aromatic hydrocarbon rings, heterocyclic rings, and rings formed by bonding and/or condensation of two or more of these rings.

Specific examples of epoxy-group-containing compounds include compounds represented by the following formula.

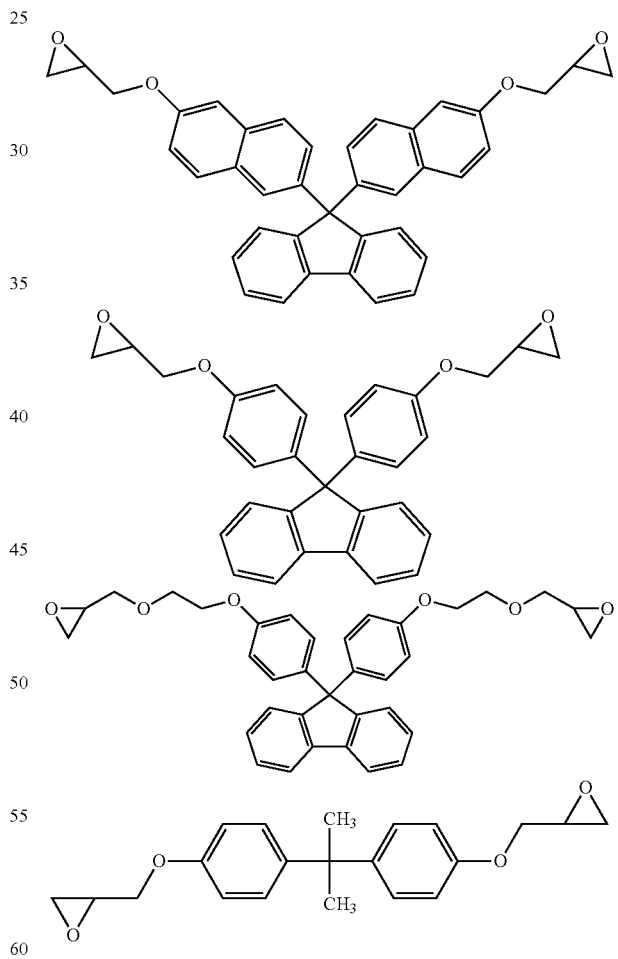

[Carboxyl-Group-Containing Compounds]

Carboxyl-group-containing compounds are not particularly limited as long as at least one carboxyl group is contained in the compound. Compounds that can react with the vinyl ether compound represented by the general formula (4) to produce polymers containing a structural unit represented by the general formula (2) or compounds represented by the general formula (3) are preferred. Compounds containing an organic group having a cyclic structure are more preferred.

When polymers containing a structural unit represented by the general formula (2) are produced, carboxyl-group-containing compounds include, for example, compounds represented by the following general formula.

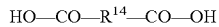
HO—CO—R$^{14}$—CO—OH (wherein R$^{14}$ represents an organic group.)

Examples of R$^{14}$ include, among groups exemplified as R$^5$, for example, divalent hydrocarbon groups, divalent heterocyclic groups, and groups formed by mutual bonding of these groups.

When compounds represented by the general formula (3) are produced, carboxyl-group-containing compounds include, for example, compounds represented by the following general formula.

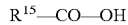
R$^{15}$—CO—OH (wherein R$^{15}$ represents an organic group.)

Examples of R$^{15}$ include, among groups exemplified as R$^{6a}$ or R$^{6b}$, for example, monovalent hydrocarbon groups, monovalent heterocyclic groups, and groups formed by mutual bonding of these groups.

Specific examples of carboxyl-group-containing compounds include compounds represented by the following formula.

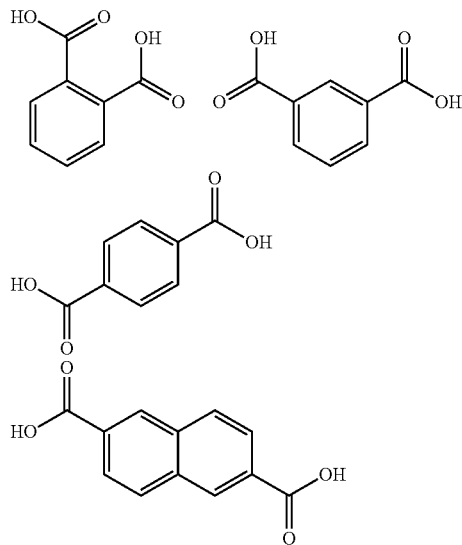

[Vinyloxy-Group-Containing Compounds]

Vinyloxy-group-containing compounds are not particularly limited as long as the vinyloxy-group-containing compounds are vinyloxy-group-containing compounds other than vinyl ether compounds represented by the general formula (4) and can react with vinyl ether compounds represented by the general formula (4). Compounds containing an organic group having a cyclic structure are preferred. Vinyloxy-group-containing compounds include, for example, compounds represented by the following general formula.

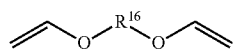

(wherein R$^{16}$ represents an organic group, provided that divalent organic groups that remain after the removal of two vinyloxy groups from vinyl ether compounds represented by the general formula (4) are excluded.)

Examples of R$^{16}$ include, among groups exemplified as R$^5$, divalent hydrocarbon groups, divalent heterocyclic groups and groups formed by mutual bonding of these groups, provided that divalent organic groups that remain after the removal of two vinyloxy groups from vinyl ether compounds represented by the general formula (4) are excluded.

Polymers containing a structural unit represented by the following general formula can be formed by reacting the vinyl ether compound represented by the general formula (4) with the vinyloxy-group-containing compound represented by the above general formula.

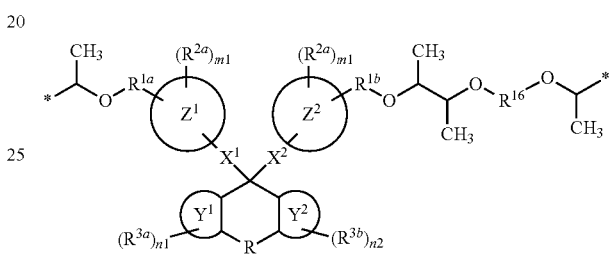

(wherein a ring Z$^1$, a ring Z$^2$, a ring Y$^1$, a ring Y$^2$, X$^1$, X$^2$, R, R$^{1a}$, R$^{1b}$, R$^{2a}$, R$^{2b}$, R$^{3a}$, R$^{3b}$, R$^{16}$, m1, m2, n1, n2, and * are as defined above.)

Vinyloxy-group-containing compounds include, for example, compounds represented by the following general formula.

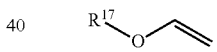

(wherein R$^{17}$ represents an organic group.)

Examples of R$^{17}$ include, among groups exemplified as R$^{6a}$ or R$^{6b}$, monovalent hydrocarbon groups, monovalent heterocyclic groups, and groups formed by mutual bonding of these groups.

Compounds represented by the following general formula can be obtained by reacting the vinyl ether compound represented by the general formula (4) with the vinyloxy-group-containing compound represented by the above general formula.

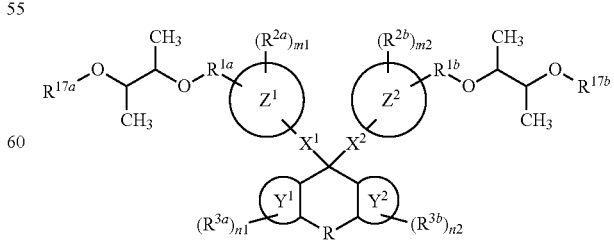

(wherein a ring a ring Z$^2$, a ring Y$^1$, a ring Y$^2$, X$^2$, R, R$^{1a}$, R$^{1b}$, R$^{2a}$, R$^{2b}$, R$^{3a}$, R$^{3b}$, m1, m2, n1, and n2 are as defined above; and $R^{17a}$ and $R^{17b}$ each independently represent an organic group. Examples of $R^{17a}$ and $R^{17b}$ include groups exemplified above as $R^{17}$.)

Specific examples of vinyloxy-group-containing compounds include compounds represented by the following formula.

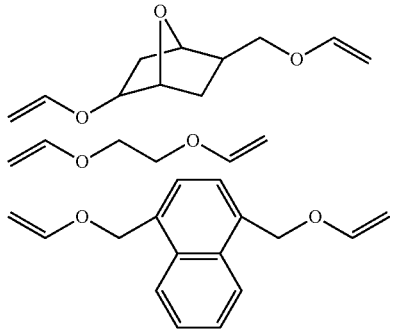

[Thiol-Group-Containing Compounds]

Thiol-group-containing compounds are not particularly limited as long as the thiol-group-containing compound can be reacted with the vinyl ether compound represented by the general formula (4). Cured products that can suppress the occurrence of birefringence and have excellent optical properties can be obtained by reacting the vinyl ether compound represented by the general formula (4) with a thiol-group-containing compound to obtain a compound containing a structural unit represented by the general formula (1) and curing the resultant compound. Thiol-group-containing compounds include, for example, compounds represented by the following general formula.

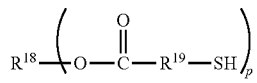

(wherein $R^{18}$ represents a p valent hydrocarbon group that optionally contains a hetero atom in the carbon chain; $R^{19}$ represents an alkylene group; and p is an integer of 1 or more.)

Examples of $R^{18}$ include mono- to hexavalent, preferably di- to tetravalent, hydrocarbon groups optionally containing hetero atoms such as oxygen, sulfur, and nitrogen atoms in the carbon chain (for example, aliphatic hydrocarbon groups, alicyclic hydrocarbon groups, aromatic hydrocarbon group, and a combination of two or more thereof). The oxygen atom may be contained as a carbonyl group in the carbon chain, and the sulfur atom may be contained as a thiocarbonyl group in the carbon chain.

Examples of $R^{19}$ include alkylene groups having 1 to 6 carbon atoms, preferably 2 to 4 carbon atoms, and specific examples thereof include methylene, ethylene, propylene, methylethylene, dimethylmethylene, and butylene groups.

p is preferably an integer of 1 to 6, more preferably an integer of 2 to 4.

Specific examples of thiol-group-containing compounds include compounds represented by the following formula.

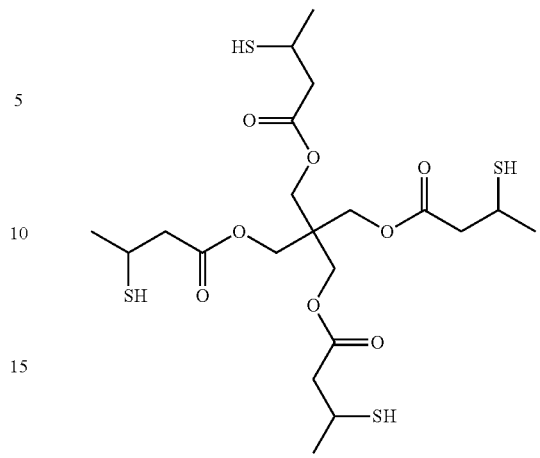

Composition

The composition according to the present invention contains at least a compound according to the present invention and a solvent.

Compound According to the Present Invention

In the composition according to the present invention, the compound according to the present invention may be used solely or in a combination of two or more thereof. The content of the compound according to the present invention is preferably 1 to 100% by mass, more preferably 10 to 100% by mass, relative to the solid content of the composition according to the present invention.

Solvent

For example, solvents usable in the production of compounds according to the present invention may be mentioned as the solvent, and specific examples thereof include hydrocarbon-based solvents (for example, aliphatic hydrocarbon-based solvents such as hexane, and aromatic hydrocarbon-based solvents such as toluene), methylene chloride, tetrahydrofuran, cyclocyclohexanone, and propylene glycol monomethyl ether acetate. The solvent may be used solely or in a combination of two or more thereof. The content of the solvent is preferably such that the solid content concentration of the composition according to the present invention is 1 to 100% by mass, more preferably 5 to 50% by mass.

Photoacid Generating Agent or Photobase Generating Agent

The composition according to the present invention may contain a photoacid generating agent or a photobase generating agent. When the composition according to the present invention contains a photoacid generating agent or a photobase generating agent, cured films obtained from the composition are likely to have a higher refractive index. Each of the photoacid generating agent and the photobase generating agent may be used solely or in a combination of two or more thereof.

Photoacid generating agents are not particularly limited as long as the compound produces an acid through the action of light, and the photoacid generating agent may be properly selected from photoacid generating agents that have hitherto been used in various applications. Photoacid generating agents include, for example, conventional acid generating agents such as onium salts, diazomethane derivatives, glyoxime derivatives, bissulfone derivatives, β-ketosulfone derivatives, disulfone derivatives, nitrobenzyl sulfonate derivatives, sulfonic acid ester derivatives, and sulfonic acid ester derivatives of N-hydroxyimide compounds. Commercially available products of photoacid generating agents include, for example, CPI-100P, CPI-110P, CPI-101A, CPI-200K, and CPI-210S (the above being tradenames of products manufactured by SAN-APRO LTD.).

Any compound that generates a base through the action of light may be used as the photobase generating agent without particular limitation, and the photobase generating agent may be properly selected from photobase generating agents that have hitherto been used in various applications. Photobase generating agents include, for example, photoactive carbamates such as triphenylmethanol, benzyl carbamate, and benzoin carbamate; amides such as o-carbamoylhydroxylamide, o-carbamoyloxime, aromatic sulfoneamide, α-lactam, and N-(2-allyethynyl)amide and other amides; oxime esters; α-aminoacetophenone; cobalt complexes; and 1-(anthraquinon-2-yl)ethylimidazole carboxylate. Commercially available products of the photobase generating agent include, for example, WPBG-018, WPBG-027, WPBG-082, WPBG-140, WPBG-165, WPBG-166, WPBG-167, WPBG-168, and WPBG-172 (the above being tradenames of products manufactured by Wako Pure Chemical Industries, Ltd.

The amount of the photoacid generating agent and the photobase generating agent used is preferably such that a desired refractive index improvement effect can be attained. The amount is properly regulated depending upon the refractive index and the like of the resultant cured film.

Other Ingredients

The composition according to the present invention may, if desired, contain photopolymerization initiators, photopolymerizable monomers, acid crosslinking substances, coloring agents, dispersing agents, sensitizing agents, and other various additives.

Optical Element Sealing Agent and Optical Element

The optical element sealing agent according to the present invention comprises a composition according to the present invention. Optical elements that are sealed with the optical element sealing agent according to the present invention include, for example, LEDs, semiconductor lasers, photodiodes, phototransistors, solar batteries, and CCDs. The optical element can be sealed by coating an optical element sealing agent according to the present invention onto the optical element and heating the coating, for example, at 120 to 300° C., preferably 150 to 250° C., to form a film. The heating time may be approximately 0.5 min to 5 hrs, particularly 1 min to 3 hrs. When a high accuracy is required, for example, in LED sealing, the heating time is preferably prolonged. When film formation is carried out as described above, the composition according to the present invention usually provides films that are colorless and transparent and have a high refractive index (a refractive index of not less than 1.54, particularly 1.60 to 1.80).

Molded Product

The molded product according to the present invention is a molded product obtained by molding a polymer containing a structural unit represented by the general formula (1). Examples of polymers containing a structural unit represented by the general formula (1) include polymers containing a structural unit represented by the general formula (2). These polymers are thermoplastic and, when heated, are easily melted. Thus, examples of molding methods for the molded products include injection molding.

EXAMPLES

Hereinafter, the present invention will be described more specifically with examples, but the scope of the present invention is not limited to these examples.

Materials

Materials used in Examples and Comparative Examples are as follows.

Vinyl Ether Compounds (Compounds Represented by the General Formula (4) and Comparative Compounds Compounds 1 and 2 represented by the following formulae were prepared as the compounds represented by the general formula (4). Further, Comparative Compound 1 represented by the following formula was prepared for comparison.

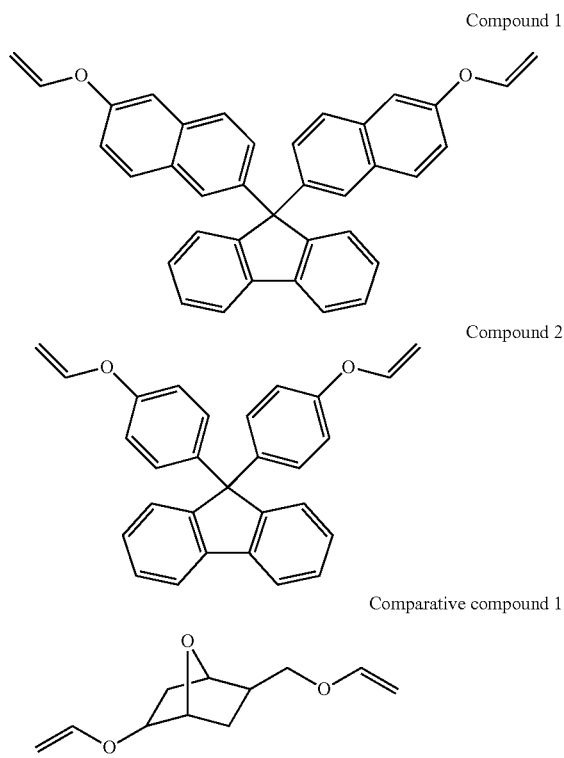

Compound 1

Compound 2

Comparative compound 1

Synthesis methods for Compounds 1 and 2 will be described below (Synthesis Examples 1 and 2). Materials used in Synthesis Examples are as follows.

[Inorganic Base]

(1) Light Ash Sodium Carbonate

Particle diameter distribution: 250 μm or more; 3% by weight

150 μm or more to less than 250 μm; 15% by weight

75 μm or more to less than 150 μm; 50% by weight

Less than 75 μm; 32% by weight

The particle diameter distribution was determined by sieving particles with sieves of 60 meshes (250 μm), 100 meshes (150 μm), and 200 meshes (75 μm) and measuring the weight of oversize particles and undersize particles obtained.

[Transition Element Compound Catalyst]

(1) Di-μ-chlorobis(1,5-cyclooctadiene)diiridium(I):[Ir(cod)Cl]$_2$

[Hydroxy Compound]

(1) 9,9'-Bis(6-hydroxy-2-naphthyl)fluorene (2) 9,9'-Bis(4-hydroxyphenyl)fluorene

[Vinyl Ester Compound]

(1) Vinyl Propionate

Synthesis Example 1

Synthesis of Compound 1

A 1000-ml reaction vessel equipped with a cooling pipe and a decanter that conducts separation of a condensate and returns an organic layer to the reaction vessel and discharges a water layer to the outside of the system was charged with di-μ-chlorobis(1,5-cyclooctadiene)diiridium(I) [Ir(cod)Cl]$_2$ (839 mg, 1.25 mmol), light ash sodium carbonate (12.7 g, 0.12 mol), 9,9'-bis(6-hydroxy-2-naphthyl)fluorene (225 g, 0.5 mol), vinyl propionate (125 g, 1.25 mol), and toluene (300 ml).

Thereafter, the temperature of the system was gradually raised while stirring with a stirring blade having a surface area of 10 cm$^2$ at a rotation speed of 250 rpm, followed by reflux. Under reflux, a reaction was allowed to proceed for 5 hrs while removing water as by-product with a decanter. The reaction solution was analyzed by gas chromatography. As a result, it was found that the conversion rate of 9,9'-bis(6-hydroxy-2-naphthyl)fluorene was 100%, and 9,9'-bis(6-vinyloxy-2-naphthyl)fluorene (Compound 1) and bis-6-naphtholfluorene monovinyl ether were produced at yields of 81% and 4%, respectively, based on 9,9'-bis(6-hydroxy-2-naphthyl)fluorene. $^1$H-NMR (CDCl$_3$): 4.47 (dd, 2H, J=1.5 Hz, 5.0 Hz), 4.81 (dd, 2H, J=3.5 Hz, 12.0 Hz), 6.71 (dd, 2H, J=6.0 Hz), 7.12-7.82 (m, 20H)

Synthesis Example 2

Synthesis of Compound 2

A 1000 ml reaction vessel equipped with a cooling pipe and a decanter that conducts separation of a condensate and returns an organic layer to the reaction vessel and discharges a water layer to the outside of the system was charged with di-μ-chlorobis(1,5-cyclooctadiene)diiridium(I) [Ir(cod)Cl]$_2$ (839 mg, 1.25 mmol), light ash sodium carbonate (12.7 g, 0.12 mol), 9,9'-bis(4-hydroxyphenyl)fluorene (186 g, 0.5 mol), vinyl propionate (125 g, 1.25 mol), and toluene (300 ml).

Thereafter, the temperature of the system was gradually raised while stirring with a stirring blade having a surface area of 10 cm$^2$ at a rotation speed of 250 rpm, followed by reflux. A reaction was allowed to proceed for 5 hrs under reflux while removing water produced as by-product with the decanter. The reaction solution was analyzed by gas chromatography. As a result, it was found that the conversion rate of 9,9'-bis(4-hydroxyphenyl)fluorene was 100%, and 9,9'-bis(4-vinyloxyphenyl)fluorene (Compound 2) and bis-4-phenolfluorene monovinyl ether were produced at yields of 72% and 9%, respectively, based on 9,9'-bis(4-hydroxyphenyl)fluorene. $^1$H-NMR (CDCl$_3$): 4.47 (dd, 2H), 4.81 (dd, 2H), 6.71 (dd, 2H), 7.12-7.82 (m, 16H)

Hydroxyl-Group-Containing Compounds

Compounds 3 to 6 represented by the following formulae were used as hydroxyl-group-containing compounds.

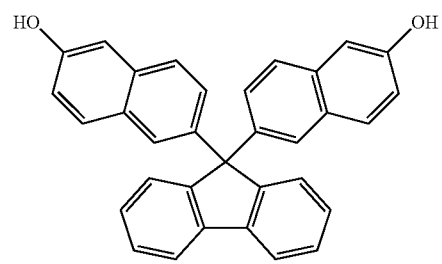

Compound 3

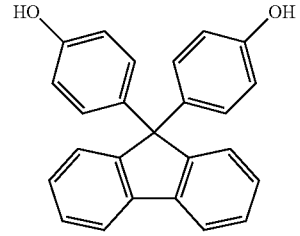

Compound 4

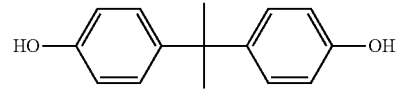

Compound 5

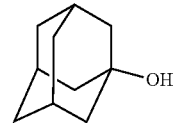

Compound 6

Photoacid Generating Agent or Photobase Generating Agent

The following PAG was used as the photoacid generating agent, and the following PBG was used as the photobase generating agent.

PAG: CPI-210S (tradename, manufactured by SAN-APRO LTD.)
PBG: WPBG-140 (tradename, manufactured by Wako Pure Chemical Industries, Ltd.
Preparation of Compounds Containing Structural Unit Derived from Vinyl Ether Compound
Reaction Between Vinyl Ether Compounds

Example 1

30 mmol of Compound 1 was dissolved in toluene in a glass flask from which water had been fully removed, after atmosphere replacement with nitrogen. Subsequently, a solution of acetic acid adduct of isobutyl vinyl ether (IBEA) in toluene and a solution of 2,4-di-tert-butylpyridine in toluene were added. The mixture was cooled to 0° C., and a solution of tin tetrabromide (SnBr$_4$) in toluene was added thereto to start polymerization. The final concentrations of Compound 1, IBEA, 2,4-di-tert-butylpyridine, and SnBr$_4$ were 0.3 M, 5 mM, 0.2 mM, and 0.5 mM, respectively. Five hours after the start of the polymerization, the reaction solution was washed with water, toluene was removed to concentrate the solution, and the resultant polymer was precipitated from methanol. The polymer thus obtained was a mixture of a linear polymer (p1) obtained by producing a new bond between carbon atoms at the α position of the vinyloxy group as a result of a reaction of Compound 1 itself and a comb-like polymer (p2) obtained by producing a new bond between at the α position and the β position of the vinyloxy group as a result of a reaction of Compound 1 itself. For the polymer thus obtained, the mass average molecular weight in terms of standard polystyrene conversion was measured by gel permeation chromatography (GPC). The results are shown in Table 1.

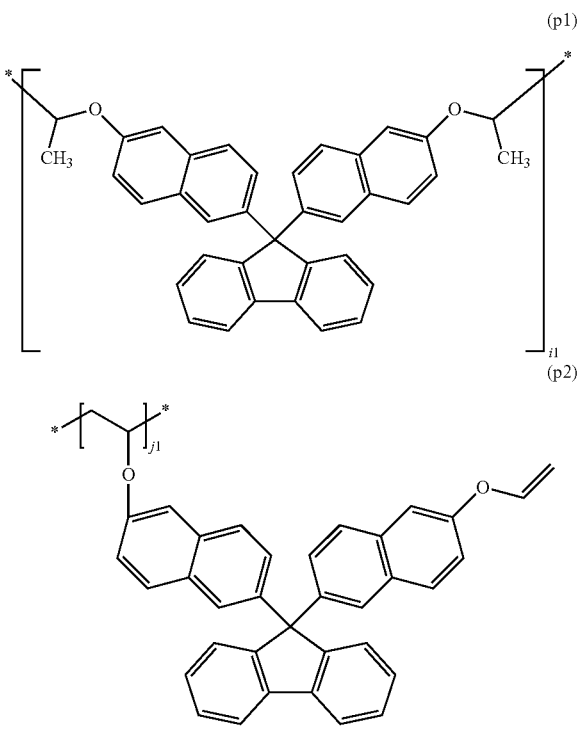

(wherein, in the formulae (p1) and (p2), * represents a bonding hand, and i1 and j1 are a number that brings the mass average molecular weight of the resultant polymer obtained as a mixture in Example 1 to 15000.)

Evaluation

The resultant polymer was dissolved in toluene to prepare a solution having a solid concentration of 20% by mass.

Refractive Index

The solution was coated on a Si wafer with a coater. The coating was heated (prebaked) on a hot plate at 100° C. for 120 sec. Thereafter, the prebaked coating was heated (postbaked) in an oven at 230° C. for 20 min to obtain a cured film (film thickness 0.25 μm). For the cured film, the refractive index (n value) and the optical absorbance index (k value) were measured at wavelengths of 248 nm and 193 nm with a refractometer. The refractive index at a wavelength of 633 nm obtained by the measurement is shown in Table 1.

Light Transmittance (Initial)

The solution was coated on a glass substrate with a coater. The coating was heated (prebaked) on a hot plate at 100° C. for 120 sec. Thereafter, the prebaked coating was heated (postbaked) in an oven at 180° C. for 20 min to form a cured film (film thickness 2.0 μm). For the cured film, the light transmittance was measured at a wavelength of 450 nm with a transmissometer. The results are shown in Table 1.

Light Transmittance (after Standing at High Temperature)

The following measurement was carried out to evaluate the heat resistance of the cured film. The solution was coated on a glass substrate with a coater. The coating was heated (prebaked) on a hot plate at 100° C. for 120 sec. Thereafter, the prebaked coating was heated (postbaked) in an oven at 180° C. for 100 hrs to form a cured film (film thickness 2.0 μm). For the cured film, the light transmittance was measured at a wavelength of 450 nm with a transmissometer. The results are shown in Table 1.

$T_{d5\%}$

The following measurement was carried out to further evaluate the heat resistance of the cured film. A cured film was formed in the same manner as described above in "Light transmittance (initial)." The cured films were heated from room temperature (about 20° C.) at a temperature rise rate of 10° C. per min to conduct a thermogravimetric analysis in the air. In the thermogravimetric analysis, a temperature at which the mass was reduced by 5% based on the mass of the cured films at the start of the analysis, $T_{d5\%}$, was measured. The results are shown in Table 1.

Example 2 and Comparative Example 1

Polymers were prepared in the same manner as in Example 1, except that Compound 2 and Comparative Compound 1 were used instead of Compound 1. Measurement of the mass average molecular weight and the evaluation of refractive index and the like were carried out on each of the polymers. The results are shown in Table 1.

The polymer obtained in Example 2 was a mixture of a linear polymer obtained by producing a new bond between carbon atoms at the α position of the vinyloxy group as a result of a reaction of Compound 2 itself and a comb-like polymer obtained by producing a new bond between at the α position and the β position of the vinyloxy group as a result of a reaction of Compound 2 itself.

Example 3

An oligomer compound was collected from a polymer obtained in the same manner as in Example 1 by silica gel column chromatography. The oligomer compound thus obtained was a mixture of a linear oligomer polymer obtained by producing a new bond between carbon atoms at the α position of the vinyloxy group as a result of a reaction of Compound 1 itself and a comb-like oligomer polymer obtained by producing a new bond between at the α position and the β position of the vinyloxy group as a result of a reaction of Compound 1 itself. Measurement of the mass average molecular weight and the evaluation of the refractive index and the like were carried out on the resultant oligomer compound in the same manner as in Example 1, except that the oligomer compound was dissolved in cyclohexanone. The results are shown in Table 1.

The measured value of the mass average molecular weight revealed that the oligomer compound corresponded to a tetramer.

TABLE 1

|  | Vinyl ether compound | Mass average molecular weight | Refractive index | Light transmittance (Initial) | Light transmittance (Standing at high temperature) | $T_{d5\%}$ (° C.) |
|---|---|---|---|---|---|---|
| Example 1 | Compound 1 | 15,000 | 1.75 | 98% | 97% | 367 |
| Example 2 | Compound 2 | 20,000 | 1.68 | 98% | 97% | 327 |

TABLE 1-continued

| | Vinyl ether compound | Mass average molecular weight | Refractive index | Light transmittance (Initial) | Light transmittance (Standing at high temperature) | $T_{d5\%}$ (° C.) |
|---|---|---|---|---|---|---|
| Comparative Example 1 | Comparative compound 1 | 5,000 | 1.51 | 98% | 35% | 184 |
| Example 3 | Compound 1 | 2,030 | 1.72 | 98% | 97% | 370 |

As is apparent from Table 1, the cured film obtained from a polymer obtained as a result of a reaction of Compound 1 itself or Compound 2 itself had a high refractive index and a high initial light transmittance. Further, the cured film maintained a high level of light transmittance even after standing at a high temperature and had high $T_{d5\%}$ and excellent heat resistance.

On the other hand, the cured film obtained from a polymer obtained as a result of a reaction of Comparative Compound 1 itself had a low refractive index although the initial transmittance was high. Further, this cured film had a low light transmittance and low $T_{d5\%}$ after standing at a high temperature and possessed poor heat resistance.

Example 4

Compound 1 was mixed with propylene glycol monomethyl ether acetate to prepare a solution having a solid content concentration of 50% by mass. This solution was refluxed at 200° C. for a polymerization reaction. For the reaction mixture after the completion of the reaction, the mass average molecular weight in terms of standard polystyrene conversion was measured by gel permeation chromatography (GPC) and was found to be not less than 20,000. This reaction mixture was cooled to room temperature and, as a result, became a transparent glass-like solid. This solid, when heated, became viscous and thermoplastic. When propylene glycol monomethyl ether was added to this solid, the solid was dissolved in the ether. From the above facts, it was confirmed that the polymer obtained as a reaction of Compound 1 itself was thermoplastic and can be molded to obtain a molded product.

Reaction of Vinyl Ether Compound with Hydroxyl-Group-Containing Compound

Example 5

0.5 g of Compound 3 that is a hydroxyl-group-containing compound was homogeneously dissolved in 10 g of cyclohexanone. 0.005 g of p-toluenesulfonic acid was homogeneously dispersed in the resultant solution. A solution obtained by homogeneously dissolving 0.5 g of Compound 1 that is a vinyl ether compound in 2.0 g of cyclohexanone was added to the resultant liquid, and the mixture was stirred at room temperature for 2 hrs to allow a reaction to proceed. After the completion of the reaction, 1.2 g of a solution of 1% by mass of triethylamine in tetrahydrofuran was added to the reaction mixture for neutralization. The resultant solution was added to 110 g of a heptane/ethyl acetate mixed solution (mass mixing ratio: 8/2) for precipitation. Wet precipitate was collected through vacuum filtration and was dried in vacuo at 45° C. for 10 hrs to obtain a compound. For the compound thus obtained, the mass average molecular weight in terms of standard polystyrene conversion was measured by gel permeation chromatography (GPC). The results are shown in Table 2.

(Evaluation)

100 parts by mass of the compound thus obtained and 0.5 part by mass of a photoacid generating agent or a photobase generating agent shown in table 2 were dissolved in cyclohexanone to prepare a solution with 20% by mass of a solid content concentration. For this solution, the refractive index, the light transmittance (initial), and the light transmittance (after standing at high temperature) were evaluated in the same manner as in Example 1. In this case, exposure to broadband light was carried out between prebaking and postbaking. The results are shown in Table 2.

Examples 6 to 15

Compounds were obtained in the same manner as in Example 5, except that a combination of a vinyl ether compound, a hydroxyl-group-containing compound, and a photoacid generating agent or a photobase generating agent as specified in Table 2 were used. Measurement of the mass average molecular weight and the evaluation of the refractive index and the like were carried out on the compounds. The results are shown in Table 2.

TABLE 2

| | Vinyl ether compound | Hydroxyl-group-containing compound | Photoacid generating agent or photobase generating agent | Mass average molecular weight | Refractive index | Light transmittance (Initial) | Light transmittance (Standing at high temperature) |
|---|---|---|---|---|---|---|---|
| Example 5 | Compound 1 | Compound 3 | PAG | 20,000 | 1.75 | 98% | 97% |
| Example 6 | Compound 1 | Compound 4 | PAG | 13,000 | 1.68 | 98% | 97% |
| Example 7 | Compound 1 | Compound 5 | PAG | 7,000 | 1.64 | 96% | 94% |
| Example 8 | Compound 1 | Compound 6 | PAG | 4,000 | 1.62 | 98% | 96% |
| Example 9 | Compound 1 | Compound 3 | PBG | 20,000 | 1.75 | 98% | 98% |
| Example 10 | Compound 2 | Compound 3 | PAG | 14,000 | 1.68 | 98% | 97% |
| Example 11 | Compound 2 | compound 4 | PAG | 8,000 | 1.65 | 98% | 97% |
| Example 12 | Compound 2 | Compound 5 | PAG | 4,000 | 1.61 | 96% | 94% |
| Example 13 | Compound 2 | Compound 6 | PAG | 4,000 | 1.58 | 97% | 96% |
| Example 14 | Compound 2 | Compound 3 | PBG | 3,000 | 1.68 | 98% | 98% |
| Example 15 | Compound 1 | Compound 3 | None | 20,000 | 1.73 | 98% | 97% |

As is apparent from Table 2, the cured film obtained from a product of a reaction between Compound 1 or 2 and any one of Compounds 3 to 6 had a high refractive index and initial light transmittance. Further, the cured films maintained the high light transmittance even after standing at a high temperature and possessed excellent heat resistance.

Further, as is apparent from a comparison of Example 5 or 9 with Example 15, the addition of the photoacid generating agent or the photobase generating agent resulted in an improvement in refractive index of the cured film.

The invention claimed is:

1. A polymer containing a structural unit represented by the following general formula (1):

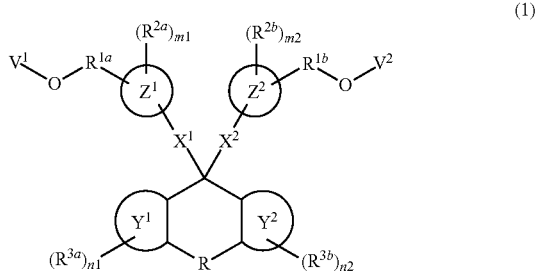

wherein a ring $Z^1$ and a ring $Z^2$, which may be the same or different, represent an aromatic hydrocarbon ring; at least one of $Z^1$ and $Z^2$ is a condensed polycyclic aromatic hydrocarbon ring; a ring $Y^1$ and a ring $Y^2$, which may be the same or different, represent an aromatic hydrocarbon ring; $X^1$ and $X^2$ each independently represent a single bond or a group represented by —S—; R represents a single bond, an optionally substituted methylene group, an ethylene group that is optionally substituted and may contain a hetero atom between two carbon atoms, a group represented by —O—, a group represented by —NH—, or a group represented by —S—; $R^{1a}$ and $R^{1b}$ each independently represent a single bond or an alkylene group having 1 to 4 carbon atoms; $R^{2a}$ and $R^{2b}$ each independently represent a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a sulfo group, or a group formed by substituting at least a part of hydrogen atoms bonded to carbon atoms contained in a monovalent hydrocarbon group, a group represented by —$OR^{4a}$, a group represented by —$SR^{4b}$, an acyl group, an alkoxycarbonyl group, a group represented by —$NHR^{4c}$, or a group represented by —$N(R^{4d})_2$ with a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a mesyloxy group, or a sulfo group; $R^{3a}$ and $R^{3b}$ each independently represent a cyano group, a halogen atom, or a monovalent hydrocarbon group; $R^{4a}$ to $R^{4d}$ each independently represent a monovalent hydrocarbon group; m1 and m2 each independently represent an integer of 0 or more; n1 and n2 each independently represent an integer of 0 to 4; $V^1$ represents a group represented by any of the following formulae (a1) to (a3); and $V^2$ represents a group represented by the following formula (a4), and

in the formula (a4), *, , and * represent a bonding hand, provided that  represents a bonding hand with an oxygen atom connected directly to $V^1$ or $V^2$ in the general formula (1), and * represents a bonding hand with an oxygen atom connected directly to $V^2$ in the general formula (1).

2. A polymer containing a structural unit represented by the following general formula (2),)

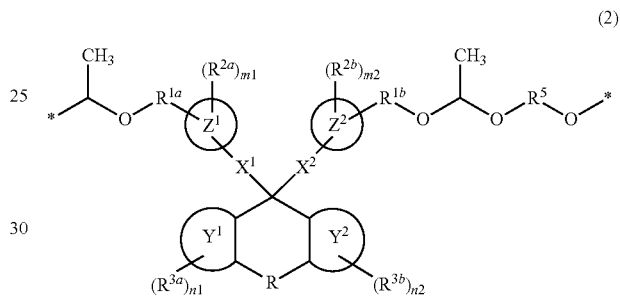

wherein a ring $Z^1$ and ring $Z^2$, which may be the same or different, represent an aromatic hydrocarbon ring; at least one of $Z^1$ and $Z^2$ is a condensed polycyclic aromatic hydrocarbon ring; a ring $Y^1$ and a ring $Y^2$, which may be the same or different, represent an aromatic hydrocarbon ring; $X^1$ and $X^2$ each independently represent a single bond or a group represented by —S—; R represents a single bond, an optionally substituted methylene group, an ethylene group that is optionally substituted and may contain a hetero atom between two carbon atoms, a group represented by —O—, a group represented by —NH—, or a group represented by —S—; $R^{1a}$ and $R^{1b}$ each independently represent a single bond or an alkylene group having 1 to 4 carbon atoms; $R^{2a}$ and $R^{2b}$ each independently represent a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a sulfo group, or a group formed by substituting at least a part of hydrogen atoms bonded to carbon atoms contained in a monovalent hydrocarbon group, a group represented by —$OR^{4a}$, a group represented by —$SR^{4b}$, an acyl group, an alkoxycarbonyl group, a group represented by —$NHR^{4c}$, or a group represented by —$N(R^{4d})_2$ with a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —NHR$^{4c}$ a group represented by —N(R$^{4d}$)$_2$, a (meth) acryloyloxy group, a mesyloxy group, or a sulfo group; R$^{3a}$ and R$^{3b}$ each independently represent a cyano group, a halogen atom, or a monovalent hydrocarbon group, R$^{4a}$ to R$^{4d}$ each independently represent a monovalent hydrocarbon group, m1 and m2 each independently represent an integer of 0 or more, and n1 and n2 each independently represent an integer of 0 to 4;* represents a bonding hand; and R$^5$ represents an organic group.

3. A composition comprising the polymer according to claim 1; and a solvent.

4. An optical element sealing agent comprising the composition according to claim 3.

5. An optical element sealed with the optical element sealing agent according to claim 4.

6. A molded product molded the polymer according to claim 1.

7. A method for producing a polymer comprising a structural unit represented by the following general formula (b3),
wherein a ring Z$^1$, a ring Z$^2$, a ring Y$^1$, a ring Y$^2$, X$^1$, X$^2$, R, R$^{1a}$, R$^{1b}$, R$^{2a}$, R$^{2b}$, R$^{3a}$, R$^{3b}$, m1, m2, n1, n2, and * are as defined in claim 1,

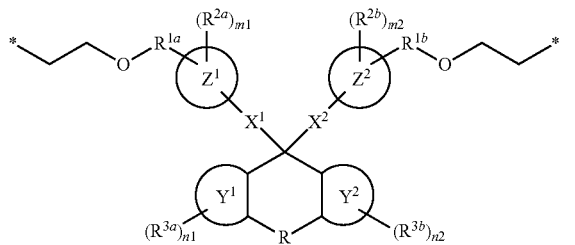
(b3)

the method comprising reacting a vinyl ether compound represented by the following general formula (4) at an α position of a vinyloxy group therein with a hydroxyl group in a hydroxyl-group-containing compound or reacting a vinyl ether compound represented by the following general formula (4) at an α position or a β position of a vinyloxy group therein with an epoxy group in an epoxy-group-containing compound:

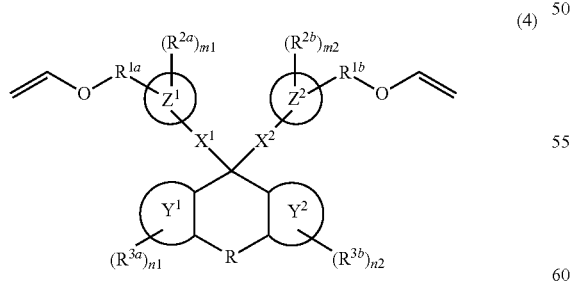
(4)

wherein a ring Z$^1$ and ring Z$^2$, which may be the same or different, represent an aromatic hydrocarbon ring; at least one of Z$^1$ and Z$^2$ is a condensed polycyclic aromatic hydrocarbon ring; a ring Y$^1$ and a ring Y$^2$, which may be the same or different, represent an aromatic hydrocarbon ring; X$^1$ and X$^2$ each independently represent a single bond or a group represented by —S—; R represents a single bond, an optionally substituted methylene group, an ethylene group that is optionally substituted and may contain a hetero atom between two carbon atoms, a group represented by —O—, a group represented by —NH—, or a group represented by —S—; R$^{1a}$ and R$^{1b}$ each independently represent a single bond or an alkylene group having 1 to 4 carbon atoms; R$^{2a}$ and R$^{2b}$ each independently represent a monovalent hydrocarbon group, a hydroxyl group, a group represented by —OR$^{4a}$, a group represented by —SR$^{4b}$, an acyl group, an alkoxycarbonyl group, a halogen atom, a nitro group, a cyano group, a mercapto group, a carboxyl group, an amino group, a carbamoyl group, a group represented by —NHR$^{4c}$, a group represented by —N(R$^{4d}$)$_2$, a (meth)acryloyloxy group, a sulfo group, or a group formed by substituting at least a part of hydrogen atoms bonded to carbon atoms contained in a monovalent hydrocarbon group, a group represented by —OR$^{4a}$, a group represented by —SR$^{4b}$, an acyl group, an alkoxycarbonyl group, a group represented by —NHR$^{4c}$, or a group represented by —N(R$^{4d}$)$_2$ with a monovalent hydrocarbon group, a hydroxyl group, a group represented by —OR$^{4a}$, a group represented by —SR$^{4b}$, an acyl group, an alkoxycarbonyl group, a halogen atom, a nitro group, a cyano group, a mercapto group, a carboxyl group, an amino group, a carbamoyl group, a group represented by —NHR$^{4c}$ a group represented by —N(R$^{4d}$)$_2$, a (meth) acryloyloxy group, a mesyloxy group, or a sulfo group; R$^{3a}$ and R$^{3b}$ each independently represent a cyano group, a halogen atom, or a monovalent hydrocarbon group, R$^{4a}$ to R$^{4d}$ each independently represent a monovalent hydrocarbon group, m1 and m2 each independently represent an integer of 0 or more, and n1 and n2 each independently represent an integer of 0 to 4.

8. The polymer according to claim 1 which is a polymer containing a structural unit represented by the following general formula (b2) or (b6)

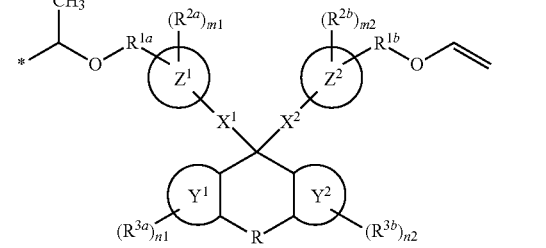
(b2)

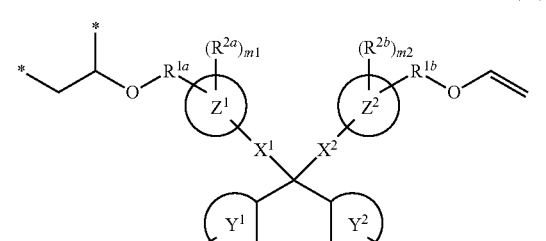
(b6)

wherein, a ring Z$^1$, a ring Z$^2$, a ring Y$^1$, a ring Y$^2$, X$^1$, X$^2$, R, R$^{1a}$, R$^{1b}$, R$^{2a}$, R$^{2b}$, R$^{3a}$, R$^{3b}$, m1, m2, n1, n2, and * are as defined in claim 1.

9. The polymer according to claim 1 which is a polymer containing a structural unit represented by the following general formula (c2)

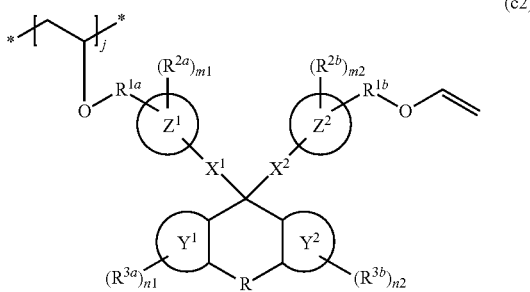

wherein, a ring $Z^1$, a ring $Z^2$, a ring $Y^1$, a ring $Y^2$, $X^1$, $X^2$, R, $R^{1a}$, $R^{1b}$, $R^{2a}$, $R^{2b}$, $R^{3a}$, $R^{3b}$, m1, m2, n1, n2, and * are as defined in claim 1 and j is a number from 2 to 600.

10. The polymer according to claim 1, wherein the ring $Z^1$ and the ring $Z^2$ each represents a naphthalene ring.

11. The polymer according to claim 1, wherein the ring $Y^1$ and the ring $Y^2$ each represents a benzene ring.

12. The polymer according to claim 1, wherein $X^1$ and $X^2$ each represents a single bond.

13. The polymer according to claim 1, wherein R represents a single bond.

14. The polymer according to claim 8, wherein the ring $Z^1$ and the ring $Z^2$ each represents a naphthalene ring.

15. The polymer according to claim 8, wherein the ring $Y^1$ and the ring $Y^2$ each represents a benzene ring.

16. The polymer according to claim 8, wherein $X^1$ and $X^2$ each represents a single bond.

17. The polymer according to claim 8, wherein R represents a single bond.

18. The polymer according to claim 9, wherein the ring $Z^1$ and the ring $Z^2$ each represents a naphthalene ring.

* * * * *